US006576772B1

(12) United States Patent
Zhang

(10) Patent No.: US 6,576,772 B1
(45) Date of Patent: Jun. 10, 2003

(54) CHIRAL PHOSPHINES, TRANSITION METAL COMPLEXES THEREOF AND USES THEREOF IN ASYMMETRIC REACTIONS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/711,635

(22) Filed: Nov. 10, 2000

Related U.S. Application Data

(60) Provisional application No. 60/164,508, filed on Nov. 10, 1999, and provisional application No. 60/187,851, filed on Mar. 8, 2000.

(51) Int. Cl.$^7$ .................................................. C07F 9/50
(52) U.S. Cl. .............................. 549/221; 549/5; 549/6; 549/7; 549/13
(58) Field of Search .............................. 549/1, 13, 5, 6, 549/7, 200, 220, 218, 219, 221

(56) References Cited

PUBLICATIONS

CA:125:222109 abs of Tetrahedron: Asymmetry by Berens et al 7(7) pp 2055–2064 1996.*
CA:124:146022 abs of J Org Chem by Berens et al 60(25) pp 8204–8 1995.*
CA:93:26505 abs of Bull Soc Chim Belg by Kagan et al 88 (11) pp 923–931 1979.*
CA:125:195812 abs of Tetrahedron Lett. by Pellon et al 37(27) pp 4713–4716 1996.*
CA:101:6263 abs of Prepr. Am. Chem Soc. Biv. Pet. Chem by Pittman et al 27(3) pp 614–23 1982.*
CA:112:177989 abs of Bull Soc Chim. Belg. by Fahrang et al 98(6) pp 387–93 1989.*
CA:107:22700 abs of J Mol Catal. by Sinou et al 36(3) pp 319–327 1986.*
CA:95:186508 abs of Proc. China U.S. Dilaterial Symp. Polym. Chem. Phys. Meeting Date 1979, by Stille pp 90–100 published 1981.*
CA:110:39137 abs of J Organometa. Chem. by Kreuzfeld et al 336(3) pp 287–92 1987.*
Organic Letters by Yan et al vol. 2, No. 2 pp 199–202 2000 (published on Web Dec. 28, 1999).*
Berens et al. "New Seven Membered Ring Chelates with Unexpected Enantioselectivity Induction in Asymmetric Hydrogenation–Hint for a Constant Relative Enantioselectivity Q for Pairs of Substrates Determined by the Structure of the Catalysts." *Tetrahedron: Asymmetry*. vol. 7, No. 7, pp. 2055–2064, 1996.

Berens et al. "Transacetalization of Diethyl Tartrate with Acetals of α–Dicarbonyl Compounds: A Simple Access to a New Class of $C_2$–Symmetric Auxiliaries and Ligands." *J. Org. Chem.* 1995, 60, 8204–8208.
Kagan et al. "Reduction Asymetrique Catalysee Par Des Complexes Des Metaux De Transition." *J. Org. Chem.* 90 (1975) 353–365.
Allevi et al. "A Practical Synthesis of ( R )– and (S)–(E)–4–Hydroxyalk–2–enals, Cytotoxic Products of the Microsomal Lipid Peroxidation." *Tetrahedron: Asymmetry*. vol. 5, No. 5, pp. 927–934, 1994.
Brunner et al. *Handbook of Enantioselective Catalysis with Transition Metal Compounds*. Weinheim, VCH, p. 359. (1980).
Ojima et al. "N–Carbamoyl–4–Diphenylphosphino–2–Diphenylphosphinomethylpyrrolidines (CAPP). Efficient new chiral ligands for asymmetric hydrogenation." *Tetrahedron Letters*. vol. 21, pp. 1051–1054, 1980.
Kagan et al. "Asymmetric catalytic reduction with transition metal complexes. I. A catalytic system of Rhodium (I) with (–)–2,3–O–Isopropylidene–2,3–dihydroxy–1,4–bis(diphenylphosphino)butane, a new Chiral Diphosphine." *J. Amer. Chem. Soc.*, 94:18, Sep. 6, 1972, pp. 6429–6433.
Zhu et al. "Highly Enantioselective Rh–Catalyzed Hydrogenations with a New Chiral 1,4–Bisphosphine Containing a Cyclic Backbone." *J. Am. Chem. Soc.* 1997, 119, pp. 1799–1800.
Selke et al. "Asymmetric Hydrogenation–Influence of the Structure of Carbohydrate Derived Catalysts on the Relative Enantioselectivity $Q_{H/Me}$ Regarding Acid and Ester Substrates and its Inversion–Selectivity Increase in Water by Amphiphiles." *Tetrahedron*. vol. 52, No. 48, pp. 15079–15102, 1996.
Kagan et al. "Synthesis of New Chiral Phosphines for Asymmetric Catalysis." *Bull. Soc. Chim. Belg.* vol. 88, No. 11, 1979.

* cited by examiner

*Primary Examiner*—Jean F. Vollano
(74) *Attorney, Agent, or Firm*—Ohlandt, Greeley, Ruggiero & Perle, L.L.P.

(57) ABSTRACT

Chiral ligands and transition metal complexes based on such chiral ligands useful in asymmetric catalysis are disclosed. The chiral ligands include (R,S,S,R)-DIOP*. The ruthenium complex reduces enamide to the corresponding amine with up to 99% enantioselectivity. The transition metal complexes of the chiral ligands are useful in asymmetric reactions such as asymmetric hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation reactions.

8 Claims, No Drawings

CHIRAL PHOSPHINES, TRANSITION METAL COMPLEXES THEREOF AND USES THEREOF IN ASYMMETRIC REACTIONS

This application claims priority from Provisional Application Ser. No. 60/164,508 filed on Nov. 10, 1999 and No. 60/187,851 filed on Mar. 8, 2000.

STATEMENT OF GOVERNMENT RIGHTS

The Government of the United States has rights in this invention puruant to Grant No. 1R01GM58832-01A1 awarded by the National Institute of Health.

BACKGROUND OF THE INVENTION

1. Field of the Invention

The present invention relates to novel chiral phosphines for applications in asymmetric catalysis. More particularly, the present invention relates to transition metal complexes of these chiral phosphine ligands. The transition metal complexes according to the present invention are useful as catalysts in asymmetric reactions.

2. Description of the Prior Art

Several families of conformationally rigid chiral bisphosphines suitable for use in transition metalatalyzed enantioselective transformations are known. The present invention discloses asymmetric catalysts based on chiral bidentate phosphines with multi-stereogenic centers in the backbone. Conformational analysis leads to the result that one of the stereochemical arrangements of the many diastereomers is the most enantioselective ligand for transition metal-catalyzed asymmetric reactions. A common feature of these ligands is that appropriate stereogenic centers in these ligands can restrict conformational flexibility of the ligands and thus the efficiency of chiral transfer can be enhanced through the ligand rigidity.

Molecular chirality plays a very important role in science and technology. The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometime has deleterious side effects. During the last few decades, asymmetric catalysis has been developed as effective method for the production of enantiomerically pure compounds.

Development of chiral phosphine ligands has played a significant role in various types of transition metal-catalyzed asymmetric synthesis (H. Brunner, W. Zettlmeier, *Handbook of Enantioselective Catalysis with Transition Metal Compounds*, Vol. 2, Ligands-References, VCH Verlagsgesellschaft, weinheim, 1993, p359). Especially, chiral diphosphines of $C_2$-symmetry are of special interest due to their high enantioselectivities in asymmetric reactions. Chiral 1,4-bisphosphines, such as, DIOP (H. B. Kagan, T.-P. Dang, *J. Am. Chem. Soc.* 1972, 94, 6429), BPPM (K. Achiwa, *J. Am. Chem. Soc.* 1976, 98, 8265; and I. Ojima, N. Yoda, *Tetrahedron Lett.* 1980, 21, 1051.), BICP (G. Zhu, P. Cao, Q. Jiang, X. Zhang, *J. Am. Chem. Soc.*, 1997, 119, 1799) have been developed for transition metal-catalyzed asymmetric catalysis.

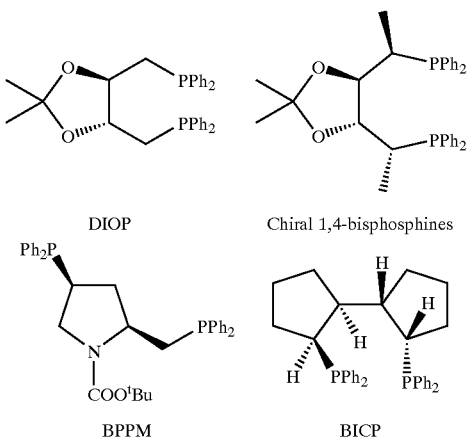

Although these ligands are effective for some asymmetric transformations, there are some areas in where these ligands are not efficient in their activity and selectivity. Thus, the design and synthesis of new chiral phosphine ligands that are effective in the more difficult asymmetric transformations remain important and challenging endeavors. The present invention discloses design and synthesis of novel chiral bisphosphines based on the conformational analysis.

The relationship between catalyst conformation and product configuration has been studied before. In general, the observed high asymmetric induction is attributed to the well define formed chiral conformation of the chelate. Based on a number of experiments, enantioselectivity with DIOP is not high in many asymmetric reactions. A possible explanation for this observation might be that the chiral centers are too far and the seven-membered chelate ring of DIOP (1) bound to transition metal (e.g., rhodium) is too conformationally flexible (the transfer of backbone chirality to the phenyl groups on the phosphine goes through a methylene group).

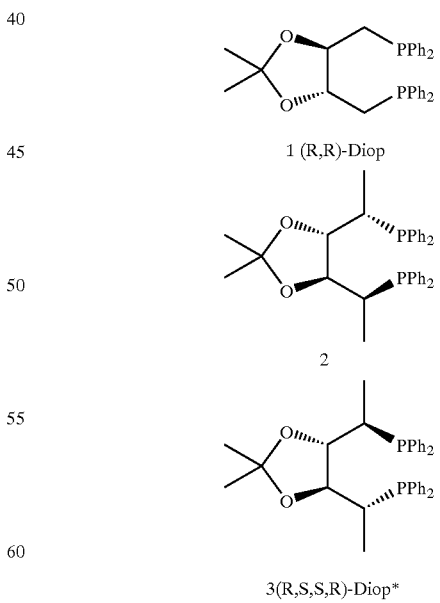

To overcome this drawback, Kagan synthesized ligand 2 in which there are two more chiral centers closer to the phosphorus atom (H. B. Kagan, J. C. Fiaud, C. Hoornaert, D. Meyer, J. C. Poulin, *Bull. Soc. Chim. Belg.* 1979, 88, 923).

Unfortunately, in this case the enantioselectivity for asymmetric hydrogenation of dehydroaminoacid was substantially lower than in the case of DIOP. We reasoned that the poor selectivity may be caused by the two newly introduced methyl groups which may have an axial position in the seven-membered chelate ring influencing enantioselectivity (R. Selke, M. Ohff, a. Riepe, *Tetrahedron* 1996, 52, 15079). This explanation suggests that the revised configuration of the two chiral centers in ligand 3 (R,S,S,R)-DIOP* (star) will force every substituent to have an equatorial position and form a well defined conformation chelated with Rh so that a high enantioselectivity can be achieved. We have found that bisphosphine 3 is a much more effective ligand than DIOP (1) and 2 for asymmetric hydrogenation reactions. This led to the conclusion that appropriate conformation of chiral ligands is the key to the high enantioselectivity, thereby providing a foundation on which the new chiral phosphines of the present invention are based.

Thus, while the hydrogenation of dehydroaminoacids (an electron-withdrawing alkene) with the Rh-based catalyst gave poor enanatioselectivity {(a) Berens, U.; Leckel, D.; Oepen, S. C. *J. Org. Chem.* 1995, 60, 8204. (b) Berens, U.; Selke, R. *Tetrahedron: Asymmetry* 1996, 7, 2055}., we have achieved outstanding results for hydrogenation and simple enamides (an electron rich alkene) with 3 (R,S,S,R)-DIOP*.

SUMMARY OF INVENTION

The present invention includes a ligand selected from the group consisting of compounds represented by I through XI:

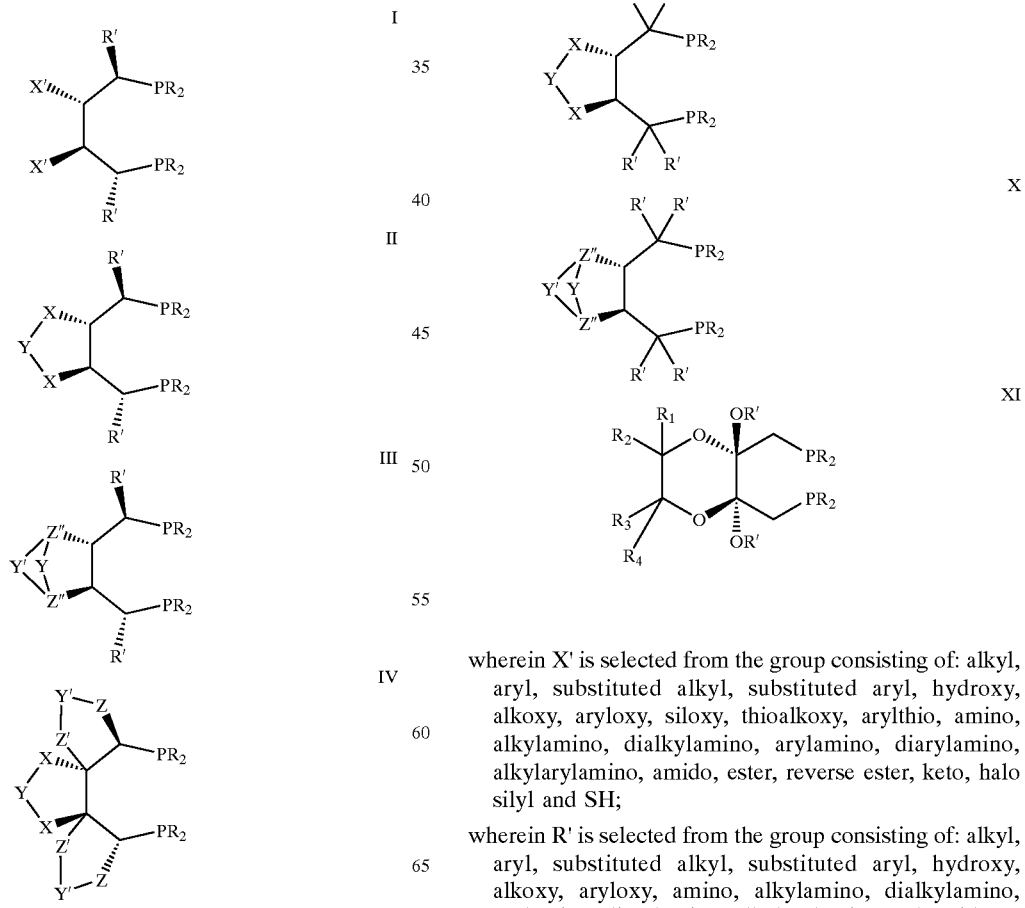

wherein X' is selected from the group consisting of: alkyl, aryl, substituted alkyl, substituted aryl, hydroxy, alkoxy, aryloxy, siloxy, thioalkoxy, arylthio, amino, alkylamino, dialkylamino, arylamino, diarylamino, alkylarylamino, amido, ester, reverse ester, keto, halo silyl and SH;

wherein R' is selected from the group consisting of: alkyl, aryl, substituted alkyl, substituted aryl, hydroxy, alkoxy, aryloxy, amino, alkylamino, dialkylamino, arylamino, diarylamino, alkylarylamino and amido;

wherein each X, Z and Z' is independently selected from the group consisting of: O, NH, NR, $CH_2$, CHR, $CR_2$, C=O, S, $SO_2$, and SO;

wherein each Z" is independently selected from the group consisting of: N, P, CH, and CR;

wherein each $R_1$, $R_2$, $R_3$ and $R_4$ is independently selected from the group consisting of: H, alkyl, aryl, substituted alkyl, substituted aryl and OR;

wherein each Y and Y' is independently selected from the group consisting of: a diol protecting group residue, O, CO, $C(OR)_2$, CH(OR), $CH_2$, CHR, $CR_2$, $CR_2$, NR, $SO_2$, —$(CH_2)_n$— wherein n is 0 or an integer from 1 to 8, —$(CH_2)_nQ(CH_2)_m$— wherein each n and m is independently an integer from 1 to 8, divalent phenyl, substituted divalent phenyl, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene, wherein the substituent in each of said substituted divalent phenyl, biphenyl, binaphthyl and ferrocene is one or more moiety each independently selected from the group consisting of: alkyl, aryl, aralkyl, alkaryl, alkenyl, akkynyl, F, Cl, Br, I, OH, OR, SH, SR, COOH, COOR, $SO_3H$, $SO_3R$, $PO_3H_2$, $PO_3HR$, $PO_3R_2$, $NH_2$, NHR, $NR_2$, $PR_2$, $AsR_2$, $SbR_2$ and nitro; and wherein each R is independently selected from the group consisting of: alkyl, aryl, substituted alkyl, substituted aryl, fluoroalkyl, perfluoroalkyl and —$CR'_2(CR'_2)_qQ(CR'_2)_pR'$ wherein each q and p is independently an integer from 1 to 8, Q is selected from the group consisting of: O, S, NR, PR, AsR, SbR, divalent aryl, divalent fused aryl, divalent 5-membered ring heterocycle and divalent fused heterocycle.

The present invention also includes a process for preparing a ligand enantiomer in high enantiomeric purity. The process comprises the steps of:

contacting an enantiomer of tartaric acid diester and a diol protecting group in the presence of an acid catalyst to produce a bis-protected tartrate diester;

contacting said bis-protected tartrate diester and a reducing agent to convert the ester functional groups in said tartaric acid diester to a diol;

converting said diol to a sulfonate ester; and displacing the sulfonate group in said sulfonate ester with lithium diphenylphosphinide to produce the ligand enantiomer.

The present invention further includes a catalyst prepared by a process comprising contacting a transition metal salt, or a complex thereof, and a ligand selected from the group consisting of compounds represented by I through XI, as described above.

The present invention still further includes a process for preparation of an asymmetric compound using a catalyst according to the present invention. The process comprises contacting a substrate capable of forming an asymmetric product by an asymmetric reaction and a catalyst prepared by a process comprising contacting a transition metal salt, or a complex thereof, and a ligand selected from compounds represented by I through XI, as described above. The transition metal complexes of the chiral ligands of the present invention produce chiral products with an extremely high enantioselectivity. For example, ruthenium complex of chiral (R,S,S,R)-DIOP* ligand reduces enamides with 99% enantioselectivity to produce the corresponding amine in a 99% ee.

DETAILED DESCRIPTION OF INVENTION

The search for new efficient chiral ligands for practical asymmetric catalytic reactions has not yet produced a universal ligand suitable for use in all asymmetric reactions. For example, hydroformylation, requires relatively electron deficient and flexible ligands for higher activity and selectivity, whereas other reactions such as hydrogenation, requires relatively electron rich and more rigid chiral ligands.

The ligand according to the present invention can be racemic, i.e., racemic mixture of enantiomers, or a non-racemic mixture of enantiomers. Preferably, the ligand according to the present invention is one of the enantiomers. When the ligand is a non-racemic mixture of enantiomers, preferably it has an optical purity of at least 85% ee, more preferably, it has an optical purity of at least 95% ee.

The various types of ligands of the present invention are described below.

The chiral ligands according to the present invention include 1,4-bisphosphines I to XI.

Ligands represented by formula I have four stereogenic centers in the backbones. Ligands represented by formula II have a ring structure connected with two middle stereogenic centers. Ligands represented by formula III have bicyclic structure in the middle of two stereogenic centers. Ligands represented by formula IV have three ring systems to control the conformation of the ligands. Ligands represented by formula V, VI and VII have a six-membered ring in the DIOP. The conformation is controlled by the special class of protecting groups. Ligands represented by formula VIII have two stereogenic centers in the middle, which transfers the chirality through the adjacent quarternary carbons. Ligands represented by formula IX have a ring structure with two stereogenic centers in the middle, which transfer the chirality through the adjacent quarternary carbons. Ligands represented by formula X have a bicyclic structure with two stereogenic centers in the center, which transfer the chirality through the adjacent quarternary carbons. Ligands represented by formula XI have a six-membered ring in the DIOP.

In formula IX, R' can be hydrogen when X is an NH or an NR group.

The preferred ligands of the present invention are selected from ligands represented by formulae I through XI, which include members represented by the formula L1 through L102, as depicted below:

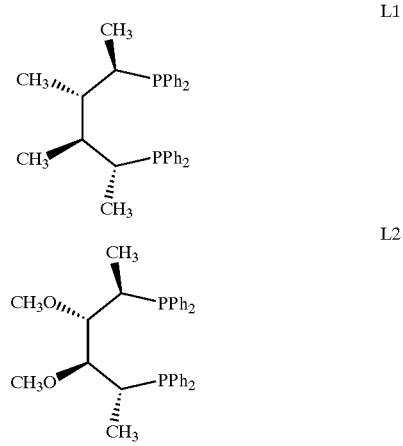

-continued
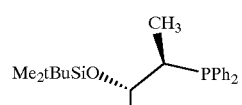 L3
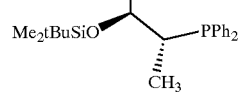 L4
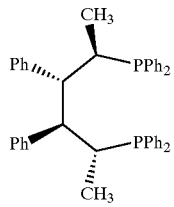 L5
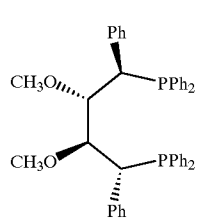 L6
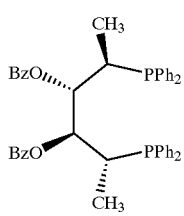 L7
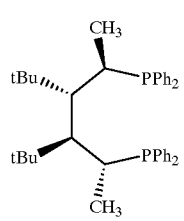 L8
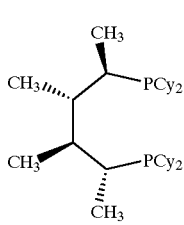 L9
-continued
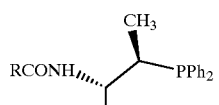 L10
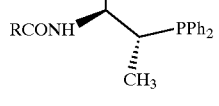 L11
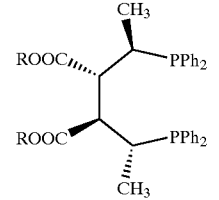 L12
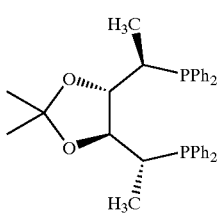 L13
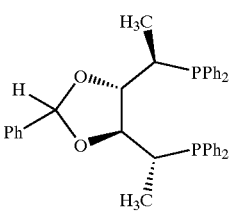 L14
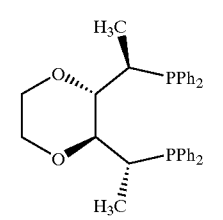 L15
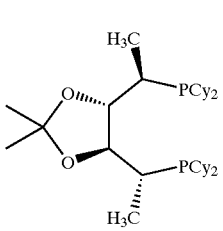 L16
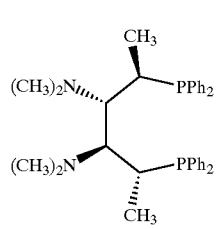
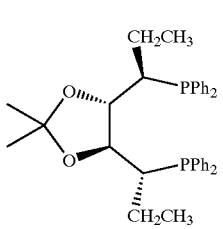

-continued
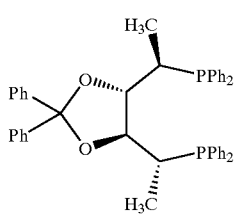
L17
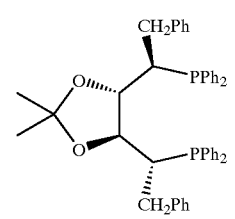
L18
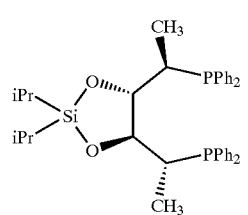
L19
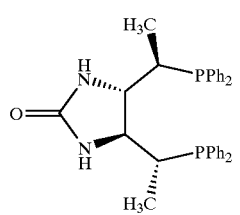
L20
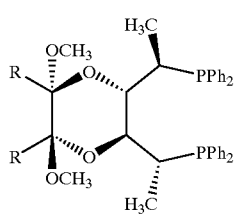
L21
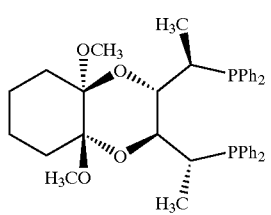
L22
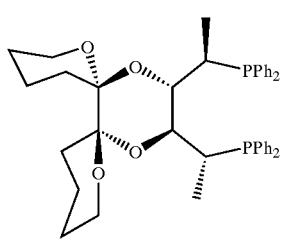
L23
-continued
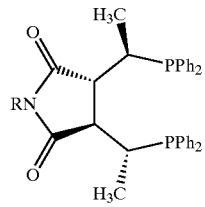
L24
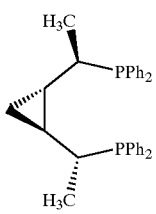
L25
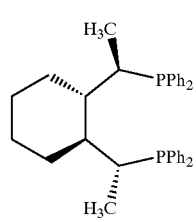
L26
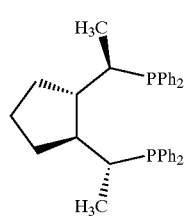
L27
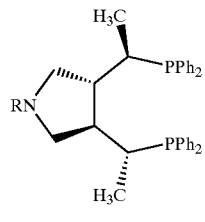
L28
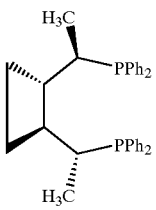
L29
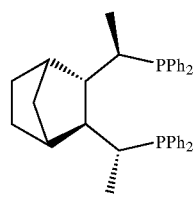
L30

-continued
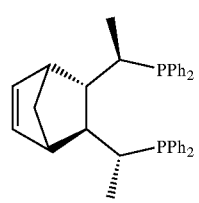 L31
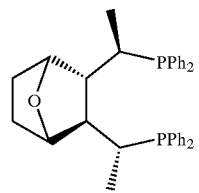 L32
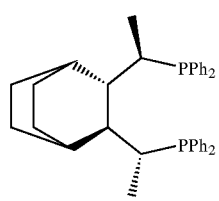 L33
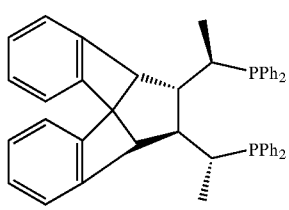 L34
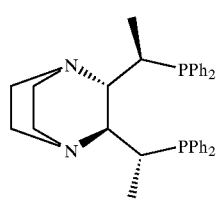 L35
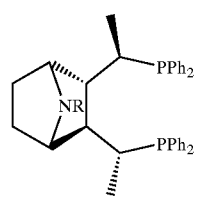 L36
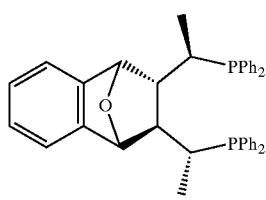 L37
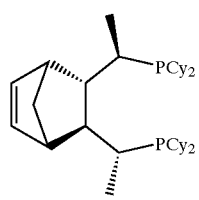 L38
-continued
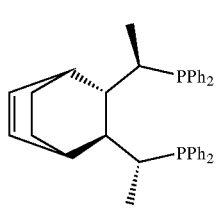 L39
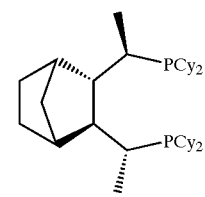 L40
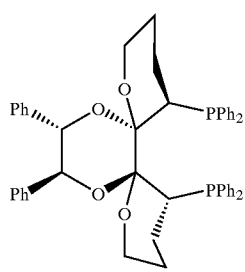 L41
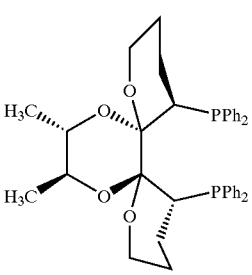 L42
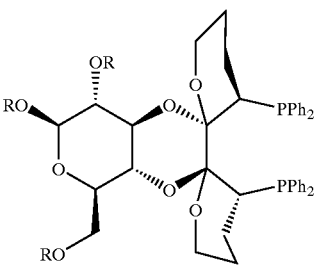 L43
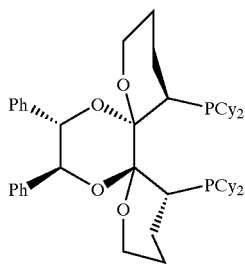 L44

-continued
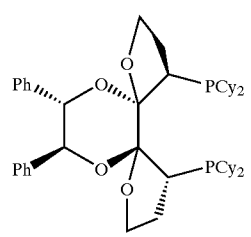 L45
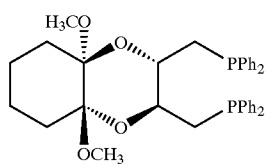 L46
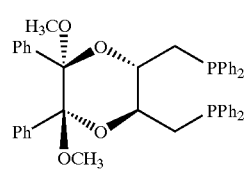 L47
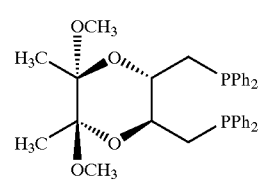 L48
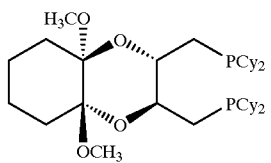 L49
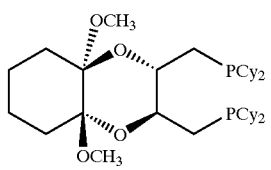 L50
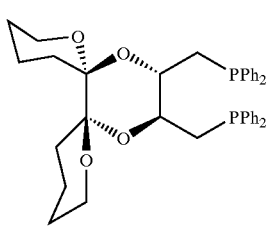 L51
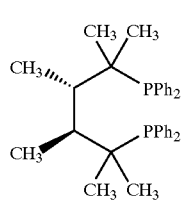 L52
-continued
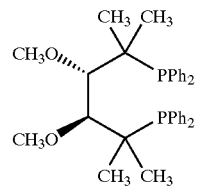 L53
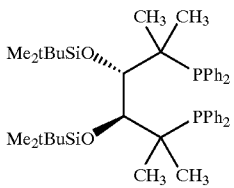 L54
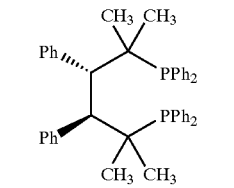 L55
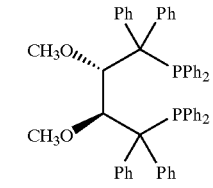 L56
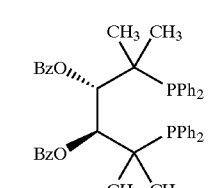 L57
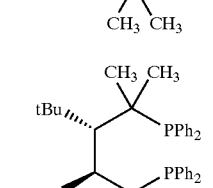 L58
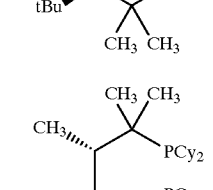 L59
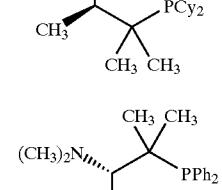 L60

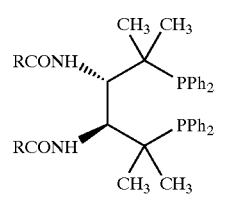 L61
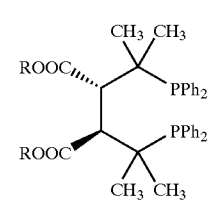 L62
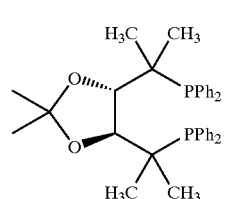 L63
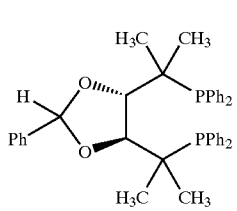 L64
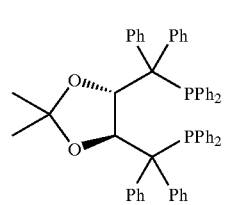 L65
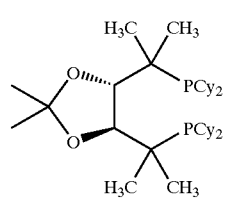 L66
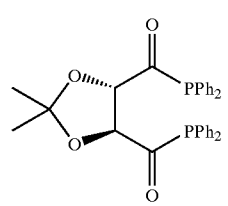 L67
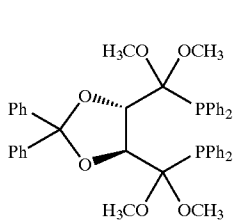 L68
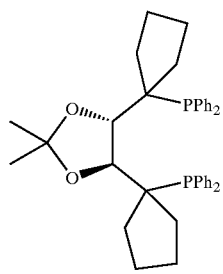 L69
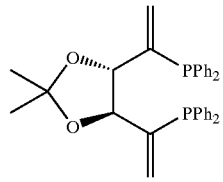 L70
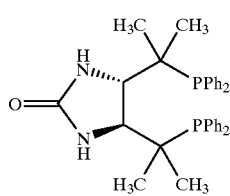 L71
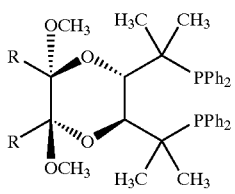 L72
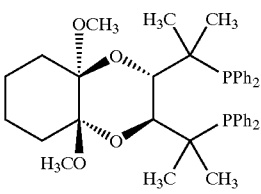 L73
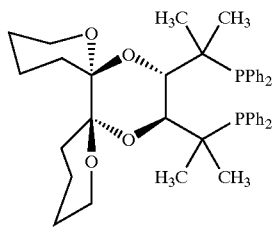 L74
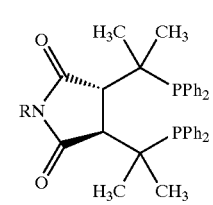 L75

L76 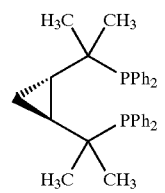
L77 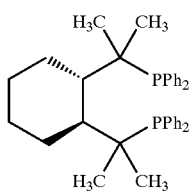
L78 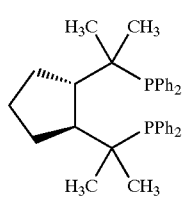
L79 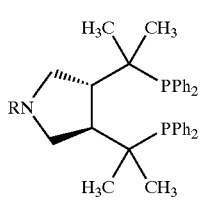
L80 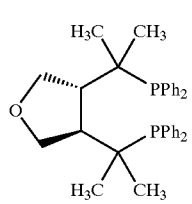
L81 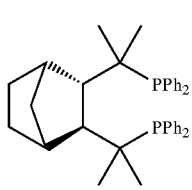
L82 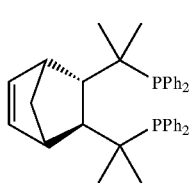
L83 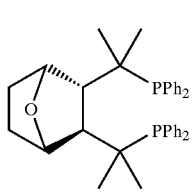
L84 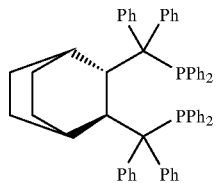
L85 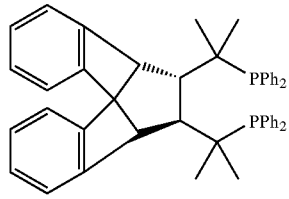
L86 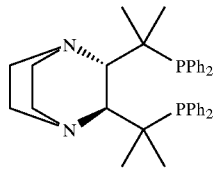
L87 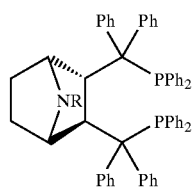
L88 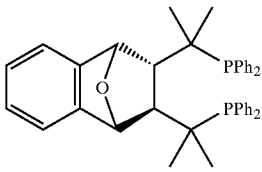
L89 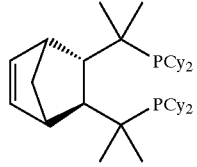
L90 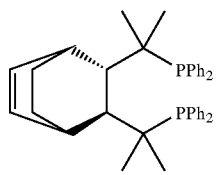
L91 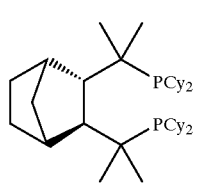
The ligand of the present invention can be used in the monomeric form or in a polymeric or copolymeric form, either as a free ligand or as a ligand supported on a support material. Preferably, the support material is either a polymer support, such as, polystyrene, polyacrylate, resin, PEG, MeO-PEG, dendritic polyester or dendritic polyenamide, or the support material is an inorganic support, such as, silica, alumina, zeolite, molecular sieve or mesoporous material. The ligand may be attached to the support material through physical interactions or it can be linked to the support material by a linker group, such as, $NH(CH_2)_nSi(OEt)_3$ wherein n=1 to 8, $CO(CH_2)_nSi(OEt)_3$, $(CH_2)_nSi(OEt)_3$, C—O, C—N and $NCF_2$ linker. The ligand may be substituted by at least one water-soluble functional group, such as, sulfuric, phosphoric, carboxylic, quaternary ammonium and MeO-PEG groups.

Organic, inorganic and polymer-supported biphase catalysts are also included. The chiral catalysts of the present invention are useful in a variety of transition metal-catalyzed asymmetric reactions.

As for the ligand, the catalyst according to the present invention can be racemic, such as, a racemic mixture of enantiomers, or it can be a non-racemic mixture of enantiomers. Preferably, the catalyst according to the present invention is one of the enantiomers. When the ligand according to the present invention is a non-racemic mixture of enantiomers, preferably it has an optical purity of at least 85% ee, more preferably, it has an optical purity of at least 95% ee.

Suitable transition metals for the preparation of the catalyst include Pt, Pd, Rh, Ru, Ir, Cu, Ni, Mo, Ti, V, Re and Mn.

The catalyst can be prepared by contacting a transition metal salt or its complex and a ligand selected from 1,4-bisphosphines I to XI. The transition metal salt or complex can be $PtCl_2$; $Pd_2(DBA)_3$; $Pd(OAc)_2$; $PdCl_2(RCN)_2$; (Pd (allyl)Cl)$_2$; $(Rh(COD)Cl)_2$; $(Rh(COD)_2)X$; $Rh(acac)(CO)_2$; $Rh(ethylene)_2(acac)$; $Rh(CO)_2Cl_2$; $Ru(RCOO)_2$ (diphosphine); Ru(methylallyl)2(diphosphine); Ru(aryl group)$X_2$(diphosphine); $RuCl_2(COD)$; $(Rh(COD)_2)X$; $RuX_2$(diphosphine); $RuCl_2$(=CHR)(PR'$_3$)$_2$; $Ru(ArH)Cl_2$; Ru(COD)(methylallyl)$_2$; $(Ir(COD)_2Cl)_2$; $(Ir(COD)_2)X$; Cu(OTf); $Cu(OTf)_2$; Cu(Ar)X; CuX; $NiX_2$; $Ni(COD)_2$; $MoO_2(acac)_2$; $Ti(OiPr)_4$; $VO(acac)_2$; $MeReO_3$; $MnX_2$ or $Mn(acac)_2$; wherein each R and R' can independently be alkyl or aryl; Ar is an aryl group; and X is a counteranion. The preferred counteranions include halogen, $BF_4$, $B(Ar)_4$ wherein Ar is 3,5-di-trifluoromethyl-1-phenyl, $ClO_4$, $SbF_6$, $CF_3SO_3$, RCOO and a mixture thereof.

The catalyst may be prepared in situ or as an isolated compound. An example of the preferred catalyst of the present invention is chiral ruthenium complex with a ligand selected from 1,4-bisphosphines I to XI.

In another aspect, the present invention includes a process for preparation of an asymmetric compound using the catalysts described above. The process includes the step of contacting a substrate capable of forming an asymmetric product by an asymmetric reaction and a catalyst prepared by contacting a transition metal salt, or a complex thereof, and a 1,4-bisphosphine ligand represented by I to XI.

Suitable asymmetric reactions include hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation.

Preferably, the asymmetric reaction is hydrogenation and the substrate to be hydrogenated is an ethylenically unsaturated compound, imine, ketone, enamine, enamide, and vinyl ester. Suitable catalysts for the hydrogenation of ketones to produce a chiral alcohol include chiral ruthenium complex with a ligand selected from 1,4-bisphosphines I to XI, particularly Ru complex of (R,S,S,R)-DIOP*.

Synthetic route to ligand (R,S,S,R)-DIOP* 3 is shown in Scheme below.

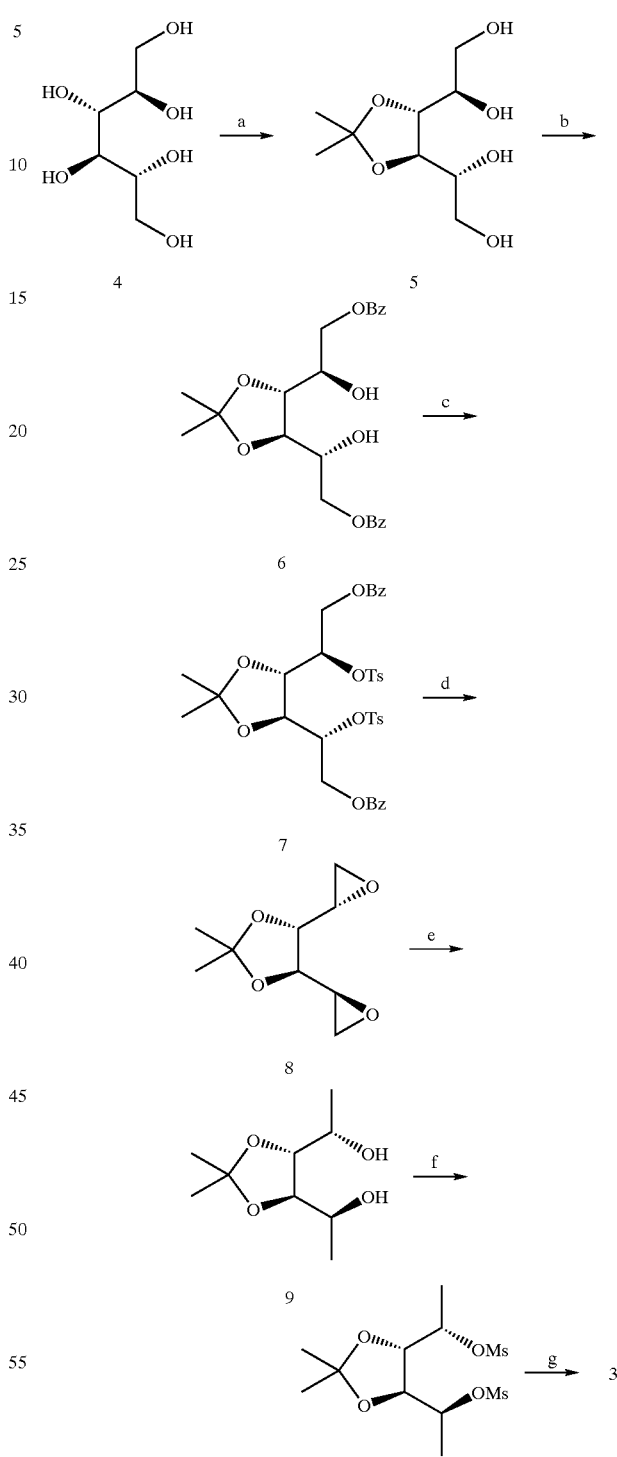

Scheme a. (i) Acetone, $H_2SO_4$; 81%; (ii). AcOH, $H_2O$, 40° C., 2.5 h; 78%.
b. BzCl, pyridine, $CH_2Cl_2$, -78° C.
c. TsCl, pyridine, DMAP, 0° C., 4 h.
d. $K_2CO_3$, $CH_3OH$, rt. 65% from 5.
e. $Et_3BH$, THF, 0° C. 83%
f. MsCl, $Et_3N$, $CH_2Cl_2$, 0° C., 96%
g. $Ph_2PH$, n-BuLi, THF, 0° C.~r.t., 67%.

Commercially available D-mannitol 4 was also used as the starting material. D-mannitol 4 is first transformed into 3,4-O-isopropylidene-D-mannitol 5 which is dibenzoylated (5→6), ditosylated (6→7). Transesterification of the benzoate of 7 liberates primary alkoxides and the concomitant intramolecular SN2 reaction occurs with inversion of configuration at $C_2$ and $C_5$. Superhydride reduction of the diepoxide 8 afford the desired diol 9. Bismesylate 10 was obtained using normal basic medium conditions in high yield. Nucleophilic attack of 10 with diphenyl phosphine in the presence of n-BuLi produced 3 as a colorless oil in 67% yield. The advantages of this synthetic route come from the versatility of diepoxide 8. Nucleophilic opening of the diepoxide 8 with various metal reagent (e.g., $CH_3MgBr$) leads to enantiomerically pure 1,4-diols with various kinds of R group inteaded of methyl group (P. Allevi, M. Anastasia, P. Ciuffreda, A. M. Sanvito, *Tetrahedron:Asymmetry* 1994, 5, 927). Furthermore, we can potentially to prepare the enantiomer of ligand 3 using the same starting material in principal. Protection of the 3,4-isopropylidene diol for ligand 2, and then reversion of the configurations of $C_3$ and $C_4$ via a Mitsunobu reaction will provide the expected diol derivatives for the enantiomer of 3.

The (R,S,S,R)-DIOP* ligand (3) was tested in the rhodium catalyzed asymmetric hydrogenation of enamide. The active catalyst employed in our study was generated in situ from a neutral Rh complex $[Rh(COD)Cl]_2$ or a cationic Rh complex $[Rh(COD)_2]SbF_6$, and 3 (R,S,S,R)-DIOP* (1:1.1). Enamide 11a was chosen as a model substrate to screen various reaction conditions. The results were listed in Table 1 together with Kagan's results using DIOP (H. B. Kagan, N. Langlois, T. P. Dang, *J. Organomet. Chem.* 1975, 90, 353). Both of neutral and cationic Rh catalyst formed in situ with 3 (R,S,S,R)-DIOP* works well on this hydrogenation, while the cationic one is a little bit better. A small hydrogen pressure effect was found for this asymmetric catalytic system. Higher pressure give better reactivity and slightly decreasing in enantioselectivity. Strongly solvent effects on the enantioselectvity and reactivity were observed. With the changing of the solvent from polar methanol to $CH_2Cl_2$ and toluene, both of the selectivity and activity dropped down dramatically. It is reasonable to assume that the most stable chiral conformation containing 3 (R,S,S,R)-DIOP* is favorable in methanol. Overall, the optimal conditions use the catalyst generated in situ from $[Rh(COD)Cl]_2$ or $[Rh(COD)_2]SbF_6$ (2 mol %) and 3 (R,S,S,R)-DIOP* (2.2 mol %) and reaction is carried out at room temperature in methanol under 10 bar of $H_2$. Under similar reaction conditions, (+)-DIOP give only 51.6% ee with the R configuration.

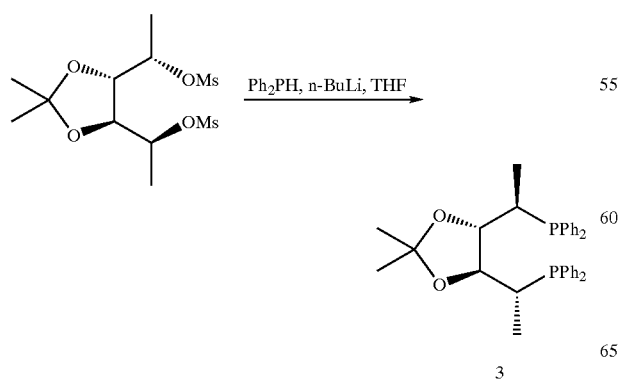

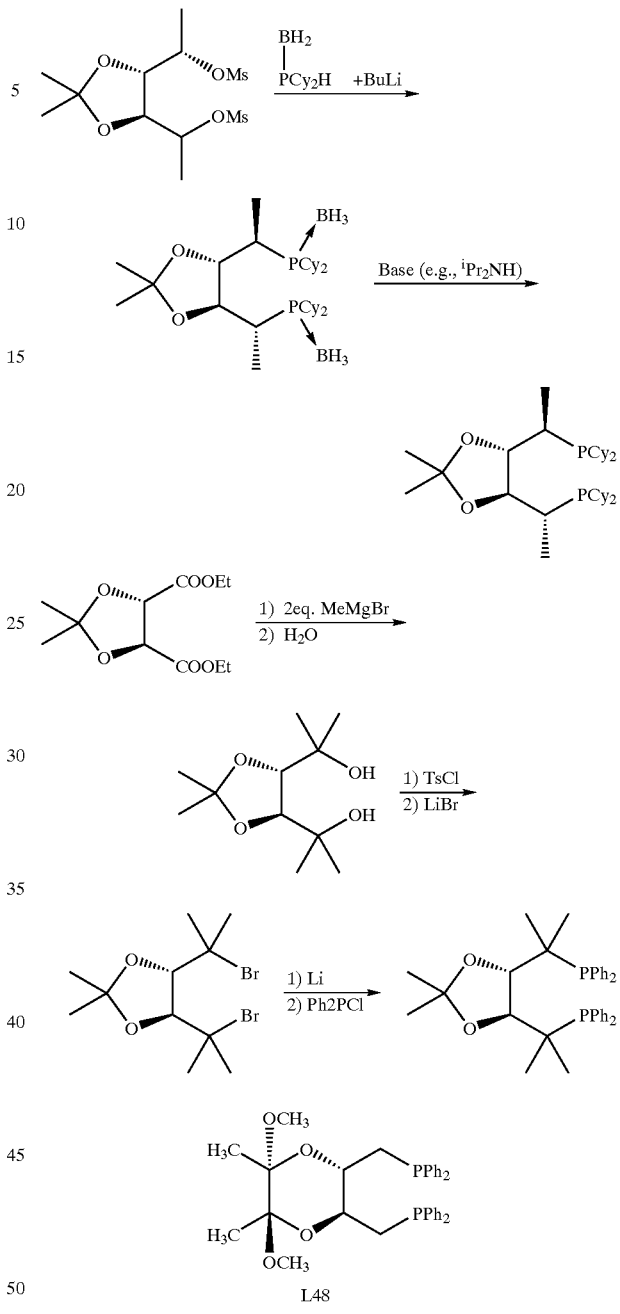

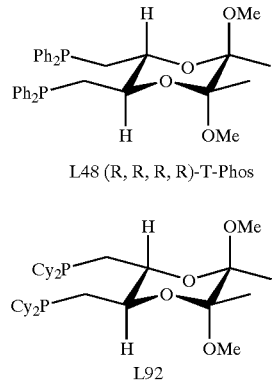

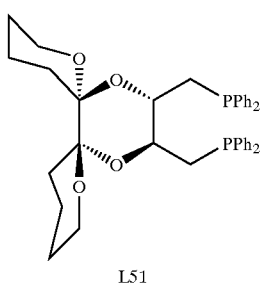

L51

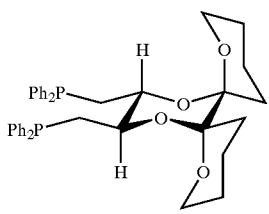

(R, R, R, R)-L51

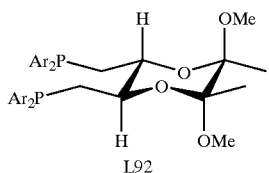

L92

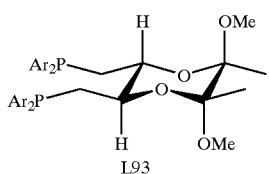

L93

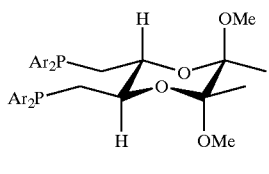

L94

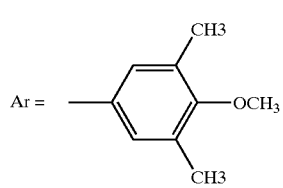

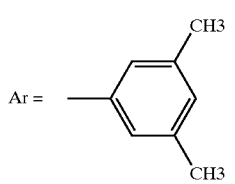

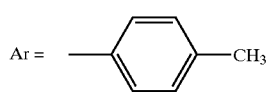

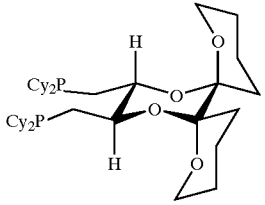

L95

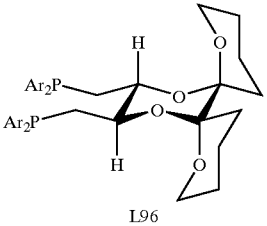

L96

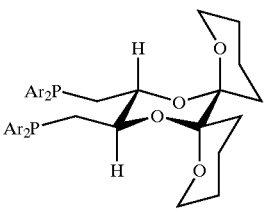

L97

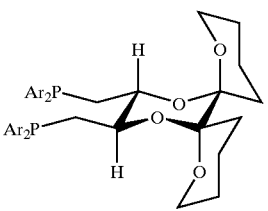

L98

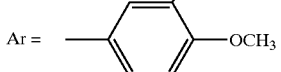

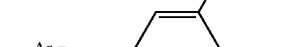

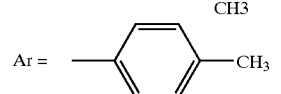

Accordingly, the present invention includes a process for preparing a ligand enantiomer in high enantiomeric purity. The process comprises the steps of:

contacting an enantiomer of tartaric acid diester and a diol protecting group in the presence of an acid catalyst to produce a bis-protected tartrate diester;

contacting said bis-protected tartrate diester and a reducing agent to convert the ester functional groups in said tartaric acid diester to a diol;

converting said diol to a sulfonate ester; and displacing the sulfonate group in said sulfonate ester with lithium diphenylphosphinide to produce the ligand enantiomer.

The scope of the asymmetric hydrogenation reaction with different substrates is shown in Table 2. High selectivities (97~>99%) have been achieved for hydrogenation of a series of α-aryl enamides using the optimal reaction conditions. An important feature of the Rh-3 (R,S,S,R)-DIOP* catalyst was observed when we extended this hydrogenation reaction to an α-aryl enamide with β-methyl group (entry 11). The hydrogenation reaction was not sensitive to the geometry of the substrates, as an isomeric mixture of (Z)- and (E)-enamides with a ratio of 1:2 in 97.3% ee under the standard reaction conditions.

Overall, β-substituted isomeric enamide mixtures and β-methyl substituted enamides with different substituent on the 1-aryl group can be reduced in high yield with high enantioselectivities (97~>99%). The enantioselectivities achieved in the Rh-3 (R,S,S,R)-DIOP* system are among the best results with those obtained with other systems.

TABLE 1

Asymmetric Hydrogenation of Enamide 11-a by a Rhodium-bisphosphine Complex[a]

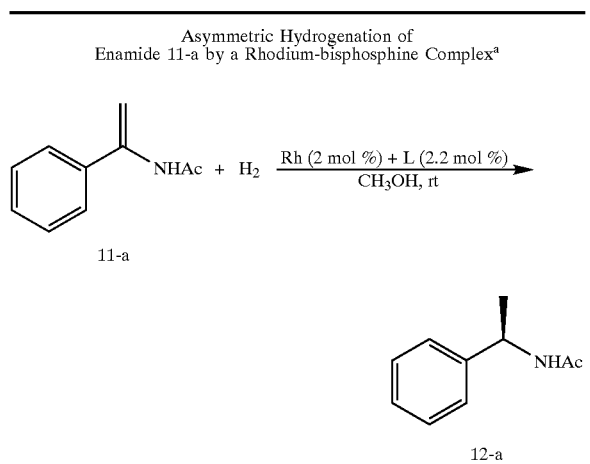

| Entry | Catalyst | Solvent | $H_2$ (bar) | ee (%)[b] | Config[c] |
|---|---|---|---|---|---|
| 1[d] | [RhCl($C_2H_4$)$_2$]$_2$/(+)-Diop | EtOH | 1.1 | 42.5[e] | R |
| 2[d] | [RhCl($C_2H_4$)$_2$]$_2$/(+)-Diop | EtOH/benzene (2/1) | 1.1 | 45[e] | R |
| 3[d] | [RhCl($C_2H_4$)$_2$]$_2$/(+)-Diop | benzene | 1.1 | 44[e] | S |
| 4[d,f] | [Rh(COD)(+)-Diop]$ClO_4$ | EtOH | 1.1 | 38.5[e] | R |
| 5[d,f] | [Rh(COD)(+)-Diop]$ClO_4$ | benzene | 1.1 | 68[e] | R |
| 6[g] | [Rh(COD)Cl]$_2$/3 | MeOH | 1.1 | 94.0 | R |
| 7 | [Rh(COD)Cl]$_2$/3 | MeOH | 10 | 97.8 | R |
| 8 | [Rh(COD)Cl]$_2$/3 | MeOH | 50 | 91.6 | R |
| 9 | [Rh(COD)Cl]$_2$/3 | $CH_2Cl_2$ | 10 | 31.5 | R |
| 10 | [Rh(COD)Cl]$_2$/3 | toluene | 10 | 5.4 | R |
| 11[g] | [Rh(COD)$_2$]$SbF_6$/3 | MeOH | 1.1 | 98.8 | R |
| 12 | [Rh(COD)$_2$]$SbF_6$/3 | MeOH | 10 | 98.3 | R |
| 13 | [Rh(COD)$_2$]$SbF_6$/3 | MeOH | 50 | 97.2 | R |
| 14[h] | [Rh(COD)$_2$]$SbPF_6$/(+)-Diop | MeOH | 1.1 | 51.6 | R |

[a]The reaction was carried out at rt under suitable psi of $H_2$ for 60 h. The catalyst was made in situ by stirring a solution of Rh precursor and the bisphosphine ligand in solvent 3 mL {[substrate (0.25 mmol, 0.083 M)/[Rh]/L = 1:0.02:0.022]}. The reaction went with >99% conversion. Otherwise stated
[b]Enantiomeric excesses were determined by chiral GC using a Supelco Chiral Select 1000 (0.25 mm x 15 m) column.
[c]The absolute configuration was assigned by comparison of optical rotation with reported data.
[d]These results are from reference.
[e]Optical purity.
[f]Preformed catalyst was used.
[g]Entries 6 and 11 with 20%, 35% conversion based on GC, respectively.
[h]With >99% conversion in 24 h.

TABLE 2

Asymmetric Hydrogenation of Enamide 11 by a Rhodium-3 Complex[a]

| Entry | Ar | R | Rh | ee (%)[b] |
|---|---|---|---|---|
| 1 | $C_6H_5$ | H | [Rh(COD)Cl]$_2$ | 97.8 |
| 2 | $C_6H_5$ | H | [Rh(COD)$_2$]$SbPF_6$ | 98.3 |
| 3 | p-$CF_3C_6H_4$ | H | [Rh(COD)Cl]$_2$ | 97.6 |
| 4 | p-$CF_3C_6H_4$ | H | [Rh(COD)$_2$]$SbPF_6$ | 97.7 |
| 5 | m-$CH_3C_6H_4$ | H | [Rh(COD)Cl]$_2$ | 98.5 |
| 6 | m-$CH_3C_6H_4$ | H | [Rh(COD)$_2$]$SbPF_6$ | 98.8 |
| 7 | p-$PhC_6H_4$ | H | [Rh(COD)Cl]$_2$ | >99[c] |
| 8 | p-$PhC_6H_4$ | H | [Rh(COD)$_2$]$SbPF_6$ | >99[c] |
| 9 | 2-naphthyl | H | [Rh(COD)Cl]$_2$ | >99[c] |
| 10 | 2-naphthyl | H | [Rh(COD)$_2$]$SbPF_6$ | 99.0[c] |
| 11 | $C_6H_5$ | $CH_3$ | [Rh(COD)$_2$]$SbPF_6$ | 97.3 |
| 12 | $C_6H_5$ | i-propyl | [Rh(COD)$_2$]$SbPF_6$ | 99.0 |
| 13 | $C_6H_5$ | Bn | [Rh(COD)$_2$]$SbPF_6$ | 98.6[c] |
| 14 | p-$CF_3C_6H_4$ | $CH_3$ | [Rh(COD)$_2$]$SbPF_6$ | 98.3 |
| 15[d] | p-$MeOC_6H_4$ | $CH_3$ | [Rh(COD)$_2$]$SbPF_6$ | 98.0[c] |
| 16 | 2-naphthyl | $CH_3$ | [Rh(COD)$_2$]$SbPF_6$ | >99[c] |

[a]The reaction was carried out at rt under 10 bar of $H_2$ for 48~60 h. The catalyst was made in situ by stirring a solution of Rh precursor and the bisphosphine ligand 3 in methanol 3 mL {[substrate (0.25 mmol, 0.083 M)/[Rh]/L = 1:0.02:0.022]}. The reaction went with >99% conversion. Otherwise stated
[b]Enantiomeric excesses were determined by chiral GC using a Supelco Chiral Select 1000 (0.25 mm x 15 m) column. The R absolute configuration was assigned by comparison of optical rotation with reported data.
[c]Enantiomeric excesses were determined by chiral HPCL using a (S,S)-whelk-o1 column.
[d]With 20% conversion based on the GC analysis.

Experimental

General Methods

All reactions and manipulations were performed in a nitrogen-filled glovebox or using standard Schlenk techniques. All reagents were obtained from Aldrich or Strem and used directly. Toluene, tetrahydrofuran (THF) and hexanes were distilled from sodium benzophenone ketyl under nitrogen. Methylene chloride ($CH_2Cl_2$) was distilled from $CaH_2$. Methanol ($CH_3OH$) was distilled from Mg under nitrogen. Gas chromatography was carried out on Helwett-Packard 6890 gas chromatographs using a Chiral Select 1000 column (Dimensions: 15 m×0.25 mm), carrier gas: He (1 mL/min$^{-1}$). HPLC analysis was carried out on a Waters™ 600 chromatograph with an (S,S)-Whelk-01 column from Regis Technologies, Inc. {particle size: 5.0 μm. column dimensions: 25 cm (length)×0.46 cm (i.d.)}. $^1$H, $^{13}$C and $^{31}$P NMR were recorded on Bruker W M 360 spectrometers. Chemical shifts were reported in ppm downfield from tetramethylsilane with the solvent resonance as the internal stand or 85% $H_3PO_4$ as the external standard respectively. Optical rotation was obtained on a Perkin Elmer 241 polarimeter.

Synthesis of 3,4-O-isopropylidene-(3S,4S)-dihydroxy-(2S,5S)-hexandiol bis(methanesulfonate) 10

To a solution of 3,4-O-isopropylidene-(3S,4S)-dihydroxy-(2S,5S)-hexandiol (2.2 g, 11.6 mmol) and triethylamine (4.9 mL, 34.8 mmol) in CH$_2$Cl$_2$ (30 mL) was added dropwise a solution of methanesulfonyl chloride (2.0 mL, 25.8 mmol) in CH$_2$Cl$_2$ (10 mL) at 0° C. After 30 min at 0° C., the reaction mixture was stirred for additional 30 min at rt, then quenched by saturated aqueous ammonium chloride solution (30 mL). The aqueous layer was extracted with CH$_2$Cl$_2$ (3×30 mL) and the combined organic solution was dried over Na$_2$SO$_4$. After evaporation of the solvent, the residue was purified by a flash chromatography on silica gel eluted with CH$_2$Cl$_2$/ethyl ether (9/1) to give a colorless oil 3.85 g in 96% yield. $^1$H NMR (CDCl$_3$, 360 NHz) δ=4.82–4.76 (m, 2H), 3.99–3.96 (m, 2H), 3.03 (s, 6H), 1.45 (d, J=6.6, 6 Hz), 1.37 (s, 6H); $^{13}$C NMR (CDCl$_3$, 90.56 NHz) δ=110.14, 78.19, 76.26, 38.53, 26.75, 17.63. HRMS cacld for C$_{11}$H$_{23}$O$_8$S$_2$ (MH$^+$) 347.0834 and C$_{11}$H$_{22}$O$_8$S$_2$Na (MNa$^+$) 369.0654; found: 347.0834 and 369.0654.

Synthesis of 3,4-O-isopropylidene-(3S,4S)-dihydroxy-(2R,5R)-bis(diphenylphosphino)hexane 3 {(R,S,S,R)-DIOP*}

To a solution of diphenylphosphine (1.15 mL, 6.6 mmol) in THF (50 mL) was added n-BuLi in hexane (4.0 mL, 6.4 mmol) at −78° C. over 5 min via a syringe. The resulting orange solution was warmed to rt and stirred for 1 hr. After cooling the mixture to −78° C., 3,4-O-isopropylidene-(3S,4S)-dihydroxy-(2S,5S)-hexandiol bis(methanesulfonate) 10 (1.04 g, 3.0 mmol) in THF (20 mL) was added over 20 min. The resulting orange solution was warmed to rt and stirred overnight. The white suspension solution was hydrolyzed with saturated aqueous NH$_4$Cl solution. The aqueous layer was extracted with CH$_2$Cl$_2$ (2×30 mL) and the combined organic solution was dried over anhydrous Na$_2$SO$_4$. After removal of the solvents under reduced pressure, the residue was purified by a flash chromatography on silical gel eluted with hexanes/ethyl acetate (95/5) to give a colorless oil 1.06 g in 67% yield. $^1$H NMR (CDCl$_3$, 360 NHz) δ=7.56–7.52 (m, 8H), 7.38–7.33 (m, 12H), 3.78–3.76 (m, 2H), 2.50–2.46 (m, 2H), 1.14 (s, 6H), 0.91 (d, J=7.0 Hz, 3H), 0.87 (d, J=6.9 Hz, 3H); $^{13}$C NMR (CDCl$_3$, 90.56 NHz) δ=136.7 (d, J=14.8 Hz), 136.2 (d, J=14.3 Hz), 133.8 (d, J=8.5 Hz), 133.6 (d, J=7.8 Hz), 128.9 (d, J=1.9 Hz), 128.3 (d, J=7.2 Hz), 108.0, 31.6 (d, J=13.3 Hz), 27.4, 11.1, 11.0. $^{31}$P NMR (CDCl$_3$) δ=−6.3 ppm.

General Procedure for Asymmetric Hydrogenation

To a solution of Rhodium precursor (0.005 mmol) in methanol (3 mL) in a glovebox was added bisphosphine (0.055 mL of 0.1 M solution in toluene, 0.0055 mmol). After stirring the mixture for 10 min, the enamide (0.25 mmol) was added. The hydrogenation was performed at rt under 1.1~50 bar of hydrogen for 24~60 h. After the hydrogen was released, the reaction mixture was passed through a short silica gel column to remove the catalyst. The enantiomeric excess was measured by capillary GC or HPLC directly without any further purification. The absolute configuration of the products was determined by comparing the observed rotation with the reported value.

Asymmetric Rh-catalyzed Hydrogenation of Enamides with a 1,4-Diphenylphosphine Bearing Butane Diacetal Backbone Considerable success has been achieved in the use of chiral arylphosphine ligands in Rh-catalyzed asymmetric hydrogenation reactions in the past three decades since the report of Kagan's DIOP 1, the first chiral diphosphine for Wilkinson type catalysts. Although a lot of analogous of DIOP have been described, few of the modified DIOP produced superior results in the transition metal catalyzed reactions. We recently designed a derivative 3 of DIOP based on the chelate conformational analysis. The Rh complex of ligand 3 (R,S,S,R)-DIOP* afforded the best results in the enantioselective hydrogenation of β-substituted and β-unsubstituted enamides caused by the equatorial orientation of all substituents in the seven membered chelate ring. These results suggest that ligand 13 in which there is a deposited 1,4-dioxane six membered ring may form a more stable conformation when chelated with rhodium than DIOP 1, and may induce higher enantioselectivities for some matched substrates. The highest selectivities in hydrogenation of enamides obtained with 2 (R,S,S,R)-DIOP*. Accordingly, the selectivity of bisphosphine ligand 13 was investigated in the hydrogenation of enarnides and the results were compared with those obtained with DIOP 1.

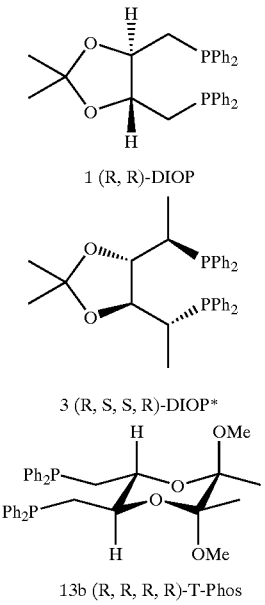

1 (R, R)-DIOP 3 (R, S, S, R)-DIOP*

13b (R, R, R, R)-T-Phos

The (2R,3R,5R,6R)-5,6-bis[(diphenylphosphanyl)methyl]-2,3-dimethoxy-2,3-dimethyl[1,4]dioxane 13b (named as T-Phos). The protected derivative 15b was formed using acetal exchange in moderate yield, while the ditosylate of diol 16b with only 53–76% yield that probably is caused by an intramolecular reaction with formation of a tetrahydrofurane derivative (Berens, U.; Leckel, D.; Oepen, S. C. *J. Org. Chem.* 1995, 60, 8204).

We found an efficient way to make 13b using Ley's one-pot methodology of tartrate ester 14b, 2,3-butanedione, trimethyl orthoformate, as well as catalytic amount of CSA (camphorsulfonic acid) as indicated in the Scheme below, to make the acetal 15b. The advantage of this approach is that only one stereoisomer was formed and isolated in high yield very easily. We synthesized the bismesylate 17b in 97% yield instead of making bistosylate. Nucleophillic attack produced the desired bisphosphine 13b smoothly in 76% yield. The other enantiomer (S,S,S,S)-13a was also made in 73% yield via the same way from D-tartrate 14a, as seen in the Scheme below.

29

Scheme

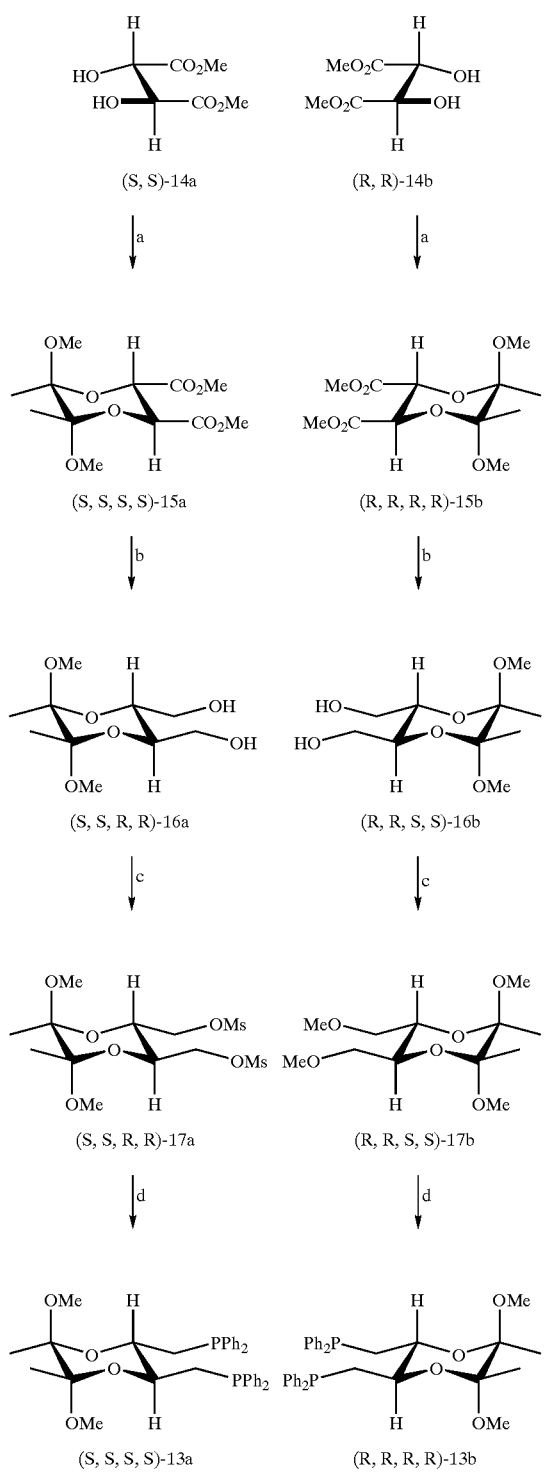

Reagents and conditions:
a) CH₃COCOCH₃ (1.2 equiv.), CSA (0.1 equiv.), CH(OCH₃)₃(3.0 equiv.), CH₃OH, reflux, 14 h;
b) LiAlH₄ (1.1 equiv.), THF, 0° C. to RT, 0.5 h;
c) MsCl, Et₃N, CH₂Cl₂, 0°C. to RT, 2 h;
d) Ph₂PH, BuLi, THF, 0° C. to RT, 12 h.

The active catalyst rhodium complex was formed in situ by mixing 1.1 equivalent 3 and [Rh(COD)₂]SbF₆ or [Rh(COD)Cl]₂ and used directly. The asymmetric hydrogenation of enamides was explored initially varying different solvent and pressure of dihydrogen to screen optimal conditions for hydrogenation of N-acetylphenylethenamine 11a. The cationic Rh complex [Rh(COD)₂]SbF₆ was found to be more effective in the selectivity than a neutral precursor [Rh(COD)Cl]₂ (Table 3, entry 2, 93.0% ee vs entry 1, 89.6% ee). As shown in Table 3, compared with methanol, toluene afforded a compareable enantioselectivity (entry 2, 93.0% ee vs entry 4, 93.9% ee), while the enantioselectivities dropped down to 87.3% ee in methylene chloride (entry 3) and 81.9% ee in THF (entry 5) respectively. Decreasing the pressure of H₂ from 75 psi to 25 psi resulted in a little bit increase of the enanotioselectivity from 93.9 to 94.5% ee (entry 6). When 13a (S,S,S,S)-T-Phos was used as the ligand, N-acetylphenylethenamine 11a was hydrogenated smoothly in 93.1% ee with reversed configuration.

It is of interest to note that the diphosphine 13b (R,R,R,R)-T-Phos resembled the ligand 1 (R,R)-DIOP, but led to an excess of the (S)-product. That is an unexpected enantioselectivity in comparison with the result for catalysts derivated from 1 (R,R)-DIOP having the analogous configuration as 13b but leading to (R)-product.

Several β-unsubstituted enanmides were also hydrogenated with the Rh-13b T-Phos catalyst (Table 4, entries 3–6) and reduced to give the enantiomerically enriched α-arylethylamine derivatives with good enantioselectivities. The substrate 11b with electron-withdrawing group (F₃C) gave a lower ee (entry 3, 82.8% ee) with the same configuration, but the electron donating substrates gave similar results as those of enamide 11a.

TABLE 3

Asymmetric Hydrogenation of Enamides by a Rhodiuim-bisphosphine Complex[a]

$$\text{11a} \xrightarrow[\text{rt}]{\text{Rh (1 mol \%) + 13 (1.1 mol \%)}} \text{(S)-12a}$$

| Entry H | Ligand | Solvent | $_2$(psi) | ee (%)[b] | Config[c] |
|---|---|---|---|---|---|
| 1[d] | 13b | MeOH | 75 | 89.6 | S |
| 2 | 13b | MeOH | 75 | 93.0 | S |
| 3 | 13b | CH₂Cl₂ | 75 | 87.3 | S |
| 4 | 13b | toluene | 75 | 93.9 | S |
| 5 | 13b | THF | 75 | 81.9 | S |
| 6 | 13b | toluene | 25 | 94.5 | S |
| 7 | 13a | toluene | 25 | 93.1 | R |

[a]The reaction was carried out at rt under suitable psi of H₂ for 24 h. The catalyst was made in situ by stirring a solution of Rh(COD)₂SbF₆ precursor and the bisphosphine ligand in solvent 4 mL {[substrate (0.5 mmol, 0.125 M)/[Rh]/3 = 1:0.01:0.011]}. The reaction went with >99% conversion. Otherwise stated
[b]Enantiomeric excesses were determined by chiral GC using a Supelco Chiral Select 1000 (0.25 mm × 15 m) column.
[c]The absolute configuration was assigned by comparison of optical rotation with reported data.
[d][Rh(COD)₂Cl]₂ was used as the precursor.

TABLE 4

Asymmetric Hydrogenation of Enamide 11 by Rhodium-13 Complex[a]

$$\text{Ar} \overset{R}{\underset{NHAc}{\diagup\!\!\diagdown}} + H_2 \xrightarrow[\text{Toluene, rt}]{\text{Rh (1 mol \%) + 13 (1.1 mol \%)}} \text{Ar} \overset{R}{\underset{NHAc}{\diagup\!\!\diagdown}}$$

11 → 12

| Entry (%) | Substrate | Ar | R | Ligand | ee[b] | Config.[c] |
|---|---|---|---|---|---|---|
| 1 | 11a | $C_6H_5$ | H | 13a | 93.1 | R |
| 2 | 11a | $C_6H_5$ | H | 13b | 94.5 | S |
| 3 | 11b | p-$CF_3C_6H_4$ | H | 13b | 82.8 | S |
| 4 | 11c | m-$CH_3C_6H_4$ | H | 13b | 95.0 | S |
| 5 | 11d | p-$PhC_6H_4$ | H | 13b | 94.2[d] | S |
| 6 | 11e | 2-naphthyl | H | 13b | 93.0[d] | S |
| 7 | 11f | $C_6H_5$ | $CH_3$ | 13a | 97.2 | R |
| 8 | 11f | $C_6H_5$ | $CH_3$ | 13b | 98.2 | S |
| 9 | 11g | $C_6H_5$ | i-propyl | 13a | 97.1 | R |
| 10 | 11g | $C_6H_5$ | i-propyl | 13b | 97.8 | S |
| 11 | 11h | $C_6H_5$ | Bn | 13a | 98.2[d] | R |
| 12 | 11h | $C_6H_5$ | Bn | 13b | 98.0[d] | S |
| 13 | 11i | p-$CF_3C_6H_4$ | $CH_3$ | 13a | 93.4 | R |
| 14 | 11i | p-$CF_3C_6H_4$ | $CH_3$ | 13b | 94.2 | S |
| 15 | 11j | p-$MeOC_6H_4$ | $CH_3$ | 13a | 98.4[d] | R |
| 16 | 11j | p-$MeOC_6H_4$ | $CH_3$ | 13b | 98.4[d] | S |
| 17 | 11k | 2-naphthyl | $CH_3$ | 13a | 97.2[d] | R |
| 18 | 11k | 2-naphthyl | $CH_3$ | 13b | 97.2[d] | S |

[a]The reaction was carried out at rt under 25 psi of $H_2$ for 24 h. The catalyst was made in situ by stirring a solution of $Rh(COD)_2SbF_6$ and the bisphosphine ligand 3 in toluene 4 mL {[substrate (0.5 mmol, 0.125 M)/[Rh]/13 = 1:0.01:0.011]}. The reaction went with >99% conversion. Otherwise stated
[b]Enantiomeric excesses were determined by chiral GC using a Supelco Chiral Select 1000 (0.25 mm x 15 m) column.
[c]The absolute configuration was assigned by comparison of optical rotation with reported data.
[d]Enantiomeric excesses were determined by chiral HPLC using a (S,S)-whelk-o1 column.

Exciting results were obtained in the hydrogenation of an α-aryl enamide with a β-methyl group. Generally, the catalyst system can hydrogenate such β-substituted enamide (Table 4, entries 7–18) more effectively than the corresponding terminal enamide substrates (Table 4, entries 1–6) with 4–12% ee higher. Even for the substrate bearing electron withdrawing group ($F_3C$) 11i, 94% ee (entries 13 and 14) was achieved. More important feature is that this hydrogenation is not sensitive to the geometry of the substrate. A E/Z mixture of β-substituted enamide was employed in all cases, for example substrate 11f, a 2:1 E/Z mixture, was hydrogenated with 98.2% ee (S) or 97.2% (R). These results are 10~14% higher than those obtained with DIOP (87% ee) or Py*-DIOP (84% ee) respectively. When R are bulky groups (iso-propyl 11g and benzyl 11h), the selectivities are still over 97% ee. Since in many cases the separations of E/Z isomers are extremely difficult, this approach is very useful to get enantiomerically enriched amines. Thus, clear the Rh-T-Phos catalytic system is very efficient in asymmetric hydrogenation of enamides. These results indicate that the six membered ring backbone in T-Phos is more conformational stable in some cases than the five membered ring in DIOP and induces higher enantioselectivity.

Synthesis of (2S,3S,5R,6R)-2,3-dimethoxy-2,3-dimethyl-5,6-bis-(((methanesulfonyl)oxy)methyl)[1,4]dioxane 17a To a solution of diol 16a (2.36 g, 10.0 mmol) and triethylamine (4.9 mL, 35.0 mmol) in $CH_2Cl_2$ (30 mL) was added drop wise a solution of methanesulfonyl chloride (2.4 mL, 30.0 mmol) in $CH_2Cl_2$ (10 mL) at 0° C. After 30 min at 0° C., the reaction mixture was stirred for additional 30 min at rt, then quenched by saturated aqueous ammonium chloride solution (30 mL). The aqueous layer was extracted with $CH_2Cl_2$ (3×30 mL) and the combined organic solution was dried over $Na_2SO_4$. After evaporation of the solvent, the residue was purified by a flash chromatography on silical gel eluted with $CH_2Cl_2$/ethyl ether (8/2) to give a white solid 3.80 g in 97% yield. Mp: 87–88° C. $[\alpha]^{24}_D=+123.6°$ (c=1.07, $CHCl_3$). $^1H$ NMR ($CDCl_3$, 360 MHz) δ=4.39–4.27 (m, 4H), 4.01–3.90 (m, 2H), 3.21 (s, 6H), 3.07 (s, 6H), 1.24 (s, 6H); $^{13}C$ NMR ($CDCl_3$, 90.56 MHz) δ=99.06, 68.68, 66.37, 48.07, 37.65, 17.14. HRMS calcd for $C_{11}H_{21}O_9S_2$ (M—$OCH_3$)$^+$: 361.0627; found: 361.0612.

Synthesis of (2S,3S,5S,6S)-5,6-bis ((diphenylphosphanyl)methyl)-2,3-dimethoxy-2,3-dimethyl-1,4-dioxane 13a To a solution of diphenylphosphine (1.90 mL, 11.0 mmol) in THF (80 mL) was added n-BuLi in hexane (6.9 mL, 11.0 mmol) at −78° C. over 5 min via a syringe. The resulting orange solution was warmed to rt and stirred for 1 h. After cooling the mixture to −78° C., bismesylate 17a (1.96 g, 5.0 mmol) in THF (20 mL) was added over 20 min. The resulting orange solution was warmed to rt and stirred overnight. The white suspension solution was hydrolyzed with saturated aqueous $NH_4Cl$ solution. The aqueous layer was extracted with $CH_2Cl_2$ (2×30 mL) and the combined organic solution was dried over anhydrous $Na_2SO_4$. After removal of the solvents under reduced pressure, the residue was purified by a flash chromatography on silical gel eluted with hexanes/ethyl acetate (95/5) to give a white solid 2.09 g in 73% yield. Mp: 70–71° C. $[\alpha]^{24}_D=+124.6°$ (c=0.98, $CHCl_3$). $^1H$ NMR ($CDCl_3$, 360 MHz) δ=7.52–7.31 (m, 20H), 3.77–3.72 (m, 2H), 3.09 (s, 6H), 2.32–2.17 (m, 4H), 1.23 (s, 6H); $^{13}C$ NMR ($CDCl_3$, 90.56 MHz) δ=139.37 (d, J=13.8 Hz), 138.15 (d, J=14.3 Hz), 133.43 (d, J=20.1 Hz), 132.37 (d, J=18.6 Hz), 129.00, 128.51 (d, J=7.4 Hz), 128.17 (d, J=6.2 Hz), 128.14, 98.91, 70.42 (m), 48.02, 30.70 (d, J=13.3 Hz), 17.40. $^{31}P$ NMR ($CDCl_3$) δ=−20.24 ppm. HRMS calcd for $C_{34}H_{39}O_4P_2$ (MH)$^+$, 573.2324 and $C_{34}H_{38}O_4P_2Na$, 595.2143; found: 573.2378 and 595.2159.

In view of the high efficiency and selectivity of Rh (I)-13 in the asymmetric hydrogenation of acyclic enamides, we have introduced a more rigid and slightly larger chiral pocket so that the dispiroketal substituents in 18 might push out the phenyl groups on the phosphorous atoms to the central metal to realize high enantioselectivity in some transition metal catalyzed reactions as ligand 13 did. Herein we report the synthesis of ligand 18 through the use of a simple, reliable strategy based on the Ley's dispoke protection procedure and an application of its Rh (I) complex in asymmetric hydrogenation of acyclic enamides.

Tartaric acid is a very important starting material for a variety of homochiral molecules, many of which retain the original $C_2$ symmetry and are used as efficient catalysts and auxiliaries in asymmetric synthesis. The new phosphine 18 with dispiroketal chiral pocket was prepared from L-(+)-dimethyl tartrate by following the procedure described in Scheme below. Reaction of excess dimethyl tartrate 19 with 3,3',4,4'-tetrahydro-6,6'-bi-2H-pyran (bis-DHP) in diethyl ethyl/CH$_2$Cl$_2$ (5:1) in the presence of hydrogen chloride at 0° C. to room temperature (12 h) gave a single diastereoisomer dispiroketal 20 in 56% yield. This product has full anomeric control at the spiro centers, but the selectivity does not stop there. Additionally, the methoxycarbonyl moieties have adopted an equatorial orientation under thermodynamic conditions. Subsequent reduction of 20 to the 1,4-diol 21 was achieved using a normal condition with LiAlH$_4$ in 85% yield. The diol 21 was transformed into the bisphosphine ligand via the intermediate dimesylate 22. Reaction of 21 with methanesulfonyl chloride in the presence of triethyl amine gave the mesylate 22 in 88% yield. Nucleophilic attack of 22 with lithium diphenylphosphinide in THF afforded the desired phosphine. The product was further purified by a short silica gel column eluted with hexanes/CH$_2$Cl$_2$/EtOAc (80:20:1) in a dry box to give a white solid in 53% yield.

Scheme

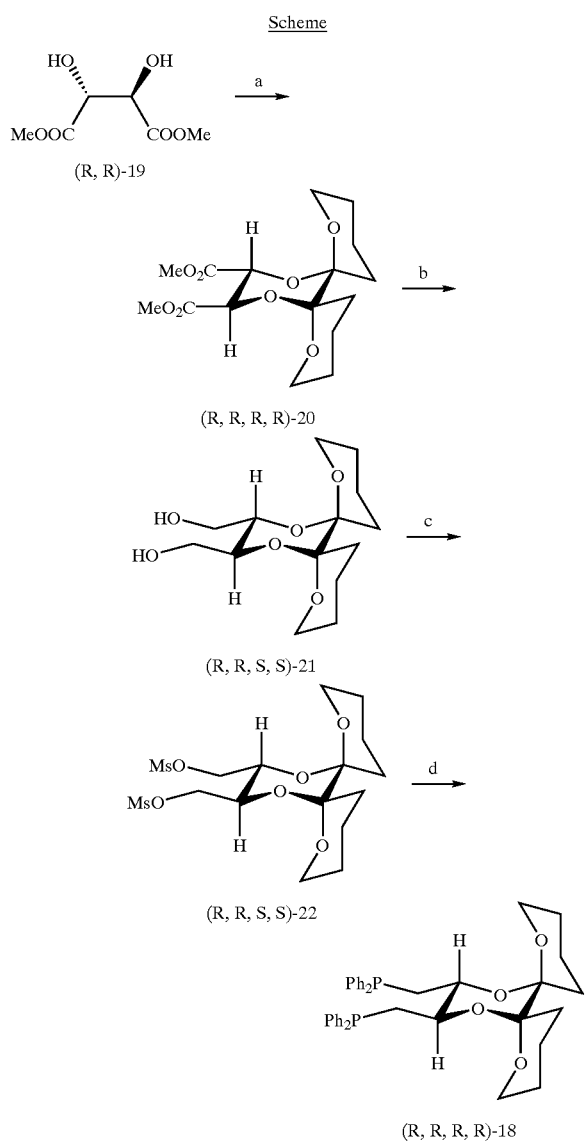

[a] Bis-DHP, HCl, Et$_2$O/CH$_2$Cl$_2$, 0° C. to rt, 12h;
[b] LiAlH$_4$ (1.1 equiv.), THF, 0° C. to rt, 12 h;
[c] MsCl, Et$_3$N, CH$_2$Cl$_2$, 0° C. to rt, 2 h;
[d] Ph$_2$PH, n-BuLi, THF, 0° C. to rt, 12 h.

The new phosphine 18 was first applied as a ligand in the rhodium catalyzed asymmetric hydrogenation of N-acetyl-1-phenylethenamine 11a. The catalysts were generated in situ by mixing chiral ligand 18 and Rh(COD)$_2$SbF$_6$ or [Rh(COD)Cl]$_2$. The cationic Rh(COD)$_2$SbF$_6$-18 complex was found to be an effective catalyst for the asymmetric hydrogenation of the typical substrate 11a. The reaction proceeded smoothly under 30 psi of H$_2$ in methanol within 24 h with 92.8% enantiomeric excess (Table 5, entry 2). However, a neutral rhodium catalyst formed in situ from phosphine 18 and [Rh(COD)Cl]$_2$ was no activity at all under similar conditions; no desired product was detected by GC (entry 1) even at higher pressure (150 psi of H$_2$). Nonpolar solvent toluene gave a similar enantioselectivity (entry 4) with 92.7% ee. In contrast, the reaction in THF (entry 5) and CH$_2$Cl$_2$ (entry 3) gave lower enantioselectivities, although complete conversions were maintained. A small hydrogen pressure effect on the selectivity was observed for this asymmetric catalytic system. Lower pressure gave slighly better enantioselectivities (entries 2, 6–8), but the reaction proceeded slow if the pressure is too low (entry 6).

TABLE 5

Asymmetric Hydrogenation of Enamide 11 by a Rhodium-18 Complex[a]

| Entry H | Solvent | $_2$(psi) | ee (%)[b] |
|---|---|---|---|
| 1[c] | MeOH | 150 | NR |
| 2 | MeOH | 30 | 92.8 |
| 3 | CH$_2$Cl$_2$ | 30 | 83.2 |
| 4 | toluene | 30 | 92.7 |
| 5 | THF | 30 | 88.9 |
| 6[d] | MeOH | 15 | 93.5 |
| 7 | MeOH | 50 | 92.3 |
| 8 | MeOH | 150 | 91.9 |

[a]The reaction was carried out at rt under suitable psi of H$_2$ for 24 h. The catalyst was made in situ by stirring a solution of Rh(COD)$_2$SbF$_6$ precursor and the bisphosphine ligand in solvent 4 mL {[substrate (0.5 mmol, 0.125 M)/[Rh]/18 = 1:0.01:0.011]}. The reaction went with >99% conversion. Otherwise
[b]Enantiomeric excesses were determined by chiral GC using a Supelco Chiral Select 1000 (0.25 mm x 15 m) column. The absolute configuration was assigned by comparison of optical rotation with reported data.
[c][Rh(COD)$_2$Cl]$_2$ was used as the precusor.
[d]32% Conversion based on GC analysis.

The Rh (I)-18 catalyst was then applied to the hydrogenation of various acyclic arylenamides under the optimized conditions: in methanol, at 30 psi of $H_2$. In all cases shown in Table 6, the hydrogenation of 11 proceeded completely to afford amides 12 in good to excellent enantioselectivities. These results show that chiral phosphine 18 has potent asymmetric induction ability similar to T-Phos and other known ligands. Worth noting is that the β-substituted substrates 11 (entries 6–11) gave superior selectivities compared with the corresponding terminal enamides 8a–e (entries 1–5), even though the substrates were E/Z mixtures.

TABLE 6

Asymmetric Hydrogenation of Enamide 11 by Rhodium-18 Complex[a]

$$\underset{11}{\text{Ar}}\overset{R}{\underset{\text{NHAc}}{\diagup\!\!\!\diagdown}} + H_2 \xrightarrow[\text{MeOH, rt}]{\text{Rh (1 mol \%) + 7 (1.1 mol \%)}} \underset{12}{\text{Ar}}\overset{R}{\underset{\text{NHAc}}{\diagup\!\!\!\diagdown}}$$

| Entry | Substrate | Ar | R | ee (%)[b] |
|---|---|---|---|---|
| 1 | 11a | $C_6H_5$ | H | 92.8 |
| 2 | 11b | p-$CF_3C_6H_4$ | H | 81.7 |
| 3 | 11c | m-$CH_3C_6H_4$ | H | 94.0 |
| 4 | 11d | p-$PhC_6H_4$ | H | 93.0[c] |
| 5 | 11e | 2-naphthyl | H | 93.2[c] |
| 6 | 11f | $C_6H_5$ | $CH_3$ | 97.2 |
| 7 | 11g | $C_6H_5$ | i-propyl | 97.7 |
| 8 | 11h | $C_6H_5$ | Bn | 97.0[c] |
| 9 | 11i | p-$CF_3C_6H_4$ | $CH_3$ | 94.2 |
| 10 | 11j | p-$MeOC_6H_4$ | $CH_3$ | 97.7[c] |
| 11 | 11k | 2-naphthyl | $CH_3$ | 97.1[c] |

[a]The reaction was carried out at rt under 30 psi of $H_2$ for 24 h. The catalyst was made in situ by stirring a solution of $Rh(COD)_2SbF_6$ and the bisphosphine ligand 18 in methanol 4 mL {[substrate (0.5 mmol, 0.125 M)/[Rh]/18 = 1:0.01:0.011]}. The reaction went with >99% conversion. Otherwise stated
[b]Enantiomeric excesses were determined by chiral GC using a Supelco Chiral Select 1000 (0.25 mm × 15 m) column. The absolute configuration was assigned by comparison of optical rotation with reported data.
[d]Enantiomeric excesses were determined by chiral HPLC using a (S,S)-whelk-o1 column.

(R,R,S,S)-1,8,13,16-Tetraoxa-dispiro[5,0,5,4]-14,15-dihydroxymethylhexadecane (21)

A solution of 20 (1.45 g, 4.21 mmol) in THF (30 mL) was added drop wise to a suspension of $LiAlH_4$ (670 mg, 17.6 mmol) in THF (100 mL) under stirring at 0° C. After 1 h stirring, the suspension was stirred for additional 12 h at ambient temperature. After cooling the mixture to 0° C., the excess of $LiAlH_4$ was decomposed by careful addition of water (0.7 mL), 15% aqueous NaOH (0.7 mL) and water (2.1 mL). Then the inorganic compounds were filtered off, and the residue was washed with $CH_2Cl_2$. The combined extracts were evaporated, and the residue was purified by flash chromatography (hexanes/EtOAc=1) to provide the product as a white solid 1.03 g in 85% yield; mp: 88–90° C. $[\alpha]^{24}_D$=–107.1° (c 0.88, $CHCl_3$). $^1$H NMR ($CDCl_3$, 360 MHz) δ3.87–3.65 (m, 10H), 2.40 (br, 2H), 1.82–1.51 (m, 12H); $^{13}$C NMR ($CDCl_3$, 90.56 MHz) δ696.10, 68.54, 62.28, 60.82, 28.23, 24.85, 18.10. HRMS calcd for $C_{14}H_{25}O_6$ ($MH^+$) and $C_{14}H_{24}O_6Na$ ($MNa^+$): 289.1651 and 311.1471; found: 289.1624 and 311.1477.

(R,R,S,S)-1,8,13,16-Tetraoxa-dispiro[5,0,5,4]-14,15-(((methanesulfonyl)oxy)methyl)hexadecane (22)

To a solution of diol 21 (600 mg, 2.08 mmol) and triethylarnine (1.5 mL, 10.0 mmol) in $CH_2Cl_2$ (30 mL) was added drop wise a solution of methanesulfonyl chloride (0.41 mL, 5.2 mmol) in $CH_2Cl_2$ (10 mL) at 0° C. After 30 min at 0° C., the reaction mixture was stirred for additional 30 min at rt, then quenched by saturated aqueous ammonium chloride solution (30 mL). The aqueous layer was extracted with $CH_2Cl_2$ (3×30 mL) and the combined organic solution was dried over $Na_2SO_4$. After evaporation of the solvent, the residue was purified by a flash chromatography on silical gel eluted with $CH_2Cl_2$/ethyl ether (9/1) to give a white solid 813 mg in 88% yield; mp: 46–7° C. $[\alpha]^{24}_D$=–73.2° (c 0.78, $CHCl_3$). $^1$H NMR ($CDCl_3$, 360 MHz) δ4.46–4.33 (m, 4H), 4.06 (m, 2H), 3.67–3.59 (m, 4H), 3.10 (s, 6H), 1.78–1.48 (m, 12H); $^{13}$C NMR ($CDCl_3$, 90.56 MHz) δ96.53, 68.81, 65.84, 60.97, 37.77, 27.95, 24.64, 17.86. HRMS calcd for $C_{16}H_{28}O_{10}S_2Na$ ($MNa^+$): 467.1022; found: 467.1018.

(R,R,R,R)-1,8,13,16-Tetraoxa-dispiro[5,0,5,4]-14,15-bis((diphenylphosphanyl)methyl)hexadecane (18)

To a solution of diphenylphosphine (0.65 mL, 3.6 mmol) in THF (60 mL) was added n-BuLi in hexane (1.6 M, 2.0 mL, 3.2 mmol) at –78° C. over 5 min via a syringe. The resulting orange solution was warmed to rt and stirred for 1 h. After cooling the mixture to –78° C., bismesylate 22 (725 mg, 1.63 mmol) in THF (20 mL) was added over 20 min. The resulting orange solution was warmed to rt and stirred overnight. The white suspension solution was hydrolyzed with saturated aqueous $NH_4Cl$ solution. The aqueous layer was extracted with $CH_2Cl_2$ (2×30 mL) and the combined organic solution was dried over anhydrous $Na_2SO_4$. After removal of the solvents under reduced preesure, the residue was purified by a flash chromatography on silical gel eluted with hexanes/$CH_2Cl_2$/ethyl acetate (80/20/1) to give a white solid 540 mg in 53% yield; mp: 105–6° C. $[\alpha]^{24}_D$=–94.3° (c 0.87, $CHCl_3$). $^1$H NMR ($CDCl_3$, 360 MHz) δ7.44–7.20 (m, 20H), 3.80–3.76 (m, 2H), 3.38–3.30 (m, 4H), 2.30–2.22 (m, 4H), 1.55–1.18 (m, 12H); $^{13}$C NMR ($CDCl_3$, 90.56 MHz) δ138.25 (d, J=8.15 Hz), 137.47 (d, J=8.97 Hz), 133.45 (d, J=19.74 Hz), 132.48 (d, J=17.93 Hz), 129.23, 128.60 (d, J=7.42 Hz), 128.46, 128.26 (d, J=6.88 Hz), 96.33, 69.85 (t, J=10.5 Hz), 60.67, 30.51 (d, J=11.61 Hz), 28.45, 24.93, 17.76. $^{31}$P NMR ($CDCl_3$) δ–18.58 ppm. HRMS calcd for $C_{38}H_{43}O_4P_2$ ($MH^+$): 625.2637; found: 625.2622.

General Procedure for Asymmetric Hydrogenation

To a solution of Rhodium precursor (0.005 mmol) in methanol (4 mL) in a glovebox was added bisphosphine 18 (0.11 mL of 0.05 M solution in toluene, 0.0055 mmol). After stirring the mixture for 10 min, the enamide (0.50 mmol) was added. The hydrogenation was performed at rt under 15~150 psi of hydrogen for 24 h. After the hydrogen was released, the reaction mixture was passed through a short silica gel column to remove the catalyst. The enantiomeric excess was measured by capillary GC or HPLC directly without any further purification. The absolute configuration of the products was determined by comparing the observed rotation with the reported value.

TABLE 7

Asymmetric Hydrogenation of Enamides by a Rhodium Complex[a]

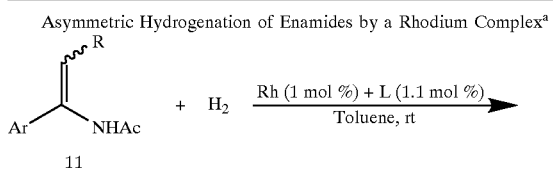

| Entry (%) | Ar | R | Ligand | ee[b] | Config.[c] |
|---|---|---|---|---|---|
| 1 | $C_6H_5$ | H | 13b | 93 | S |
| 2 | $C_6H_5$ | H | 18 | 93 | S |
| 3 | $C_6H_5$ | $CH_3$ | 13b | 98 | S |
| 4 | $C_6H_5$ | $CH_3$ | 18 | 97 | S |
| 5 | $C_6H_5$ | i-propyl | 13b | 98 | S |
| 6 | $C_6H_5$ | i-propyl | 18 | 98 | S |
| 7 | $C_6H_5$ | Bn | 13b | 98 | S |
| 8 | $C_6H_5$ | Bn | 18 | 97 | S |
| 9 | p-$CF_3C_6H_4$ | $CH_3$ | 13b | 95 | S |
| 10 | p-$CF_3C_6H_4$ | $CH_3$ | 17 | 94 | S |
| 11 | p-$MeOC_6H_4$ | $CH_3$ | 13b | 98 | S |
| 12 | p-$MeOC_6H_4$ | $CH_3$ | 18 | 98 | S |
| 13 | 2-naphthyl | $CH_3$ | 13b | 97 | S |
| 14 | 2-naphthyl | $CH_3$ | 18 | 97 | S |

[a]The reaction was carried out at rt under 45 psi of $H_2$ for 24 h. The catalyst was prepared in situ by stirring a solution of $Rh(NBD)_2SbF_6$ and the bisphosphine ligand L in methanol 4 mL {[substrate (0.5 mmol, 0.125 M)/[Rh]/L = 1:0.01:0.011]}. The reaction went with >99% conversion unless otherwise stated.
[b]Enantiomeric excesses were determined by chiral GC using a Supelco Chiral Select 1000 (0.25 mm × 15 m) column.
[c]The absolute configuration was assigned by comparison of optical rotation with reported data.
[d]Enantiomeric excesses were determined by chiral HPLC using a (S,S)-whelk-o1 column.

TABLE 8

Asymmetric Hydrogenation of Enamides by Rhodium-bisphosphine Complex[a]

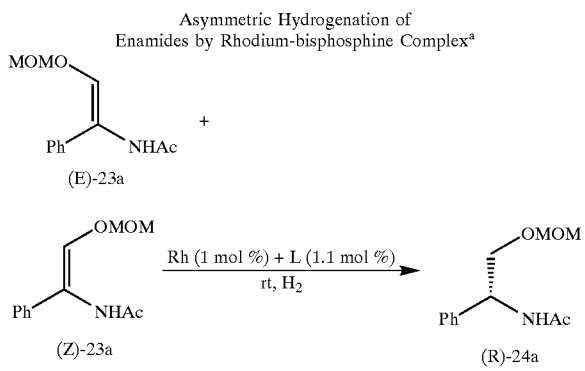

| Entry | Rh | Ligand | Solvent | $H_2$ (bar) | ee (%)[b] | Config[c] |
|---|---|---|---|---|---|---|
| 1 | $Rh(COD)_2PF_6$ | 13b | MeOH | 15 | 97 | R |
| 2 | $Rh(COD)_2PF_6$ | 13b | $CH_2Cl_2$ | 15 | 97 | R |
| 3 | $Rh(COD)_2PF_6$ | 13b | toluene | 15 | 98 | R |
| 4 | $Rh(COD)_2PF_6$ | 13b | THF | 15 | 94 | R |
| 5 | $Rh(COD)_2PF_6$ | 13b | toluene | 20 | 98 | R |
| 6 | $Rh(COD)_2PF_6$ | 13b | toluene | 10 | 97 | R |
| 7 | $Rh(COD)_2PF_6$ | 13b | $CH_2Cl_2$ | 20 | 95 | R |
| 8 | $Rh(COD)_2PF_6$ | 13b | $CH_2Cl_2$ | 10 | 94 | R |
| 9 | $Rh(COD)_2SbF_6$ | 13b | $CH_2Cl_2$ | 15 | 97 | R |

TABLE 8-continued

Asymmetric Hydrogenation of Enamides by Rhodium-bisphosphine Complex[a]

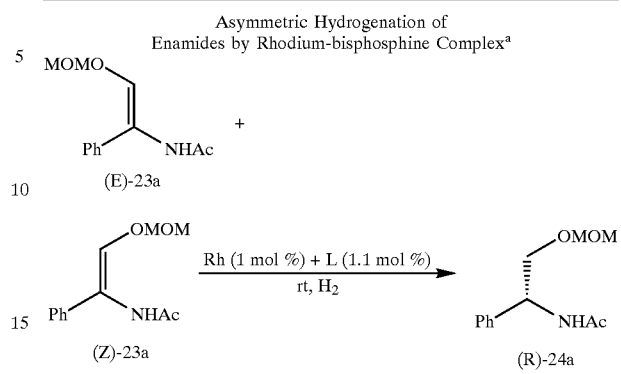

| Entry | Rh | Ligand | Solvent | $H_2$ (bar) | ee (%)[b] | Config[c] |
|---|---|---|---|---|---|---|
| 10 | $Rh(NBD)_2BF_4$ | 13b | $CH_2Cl_2$ | 15 | 95 | R |
| 11 | $Rh(NBD)_2SbF_6$ | 13b | $CH_2Cl_2$ | 15 | 98 | R |
| 12 | $Rh(NBD)_2SbF_6$ | 13b | $CH_2Cl_2$ | 15 | 96 | R |
| 13 | $Rh(NBD)_2SbF_6$ | 13b | $CH_2Cl_2$ | 15 | 87 | R |
| 14 | $Rh(NBD)_2SbF_6$ | 18 | $CH_2Cl_2$ | 15 | 97 | R |
| 15 | $Rh(NBD)_2SbF_6$ | 13a | $CH_2Cl_2$ | 15 | 98 | S |

[a]The reaction was carried out at room temperature under suitable bar of $H_2$ for 36 h. The catalyst was prepared in situ by stirring a solution of Rh precursor and the bisphosphine ligand L in solvent 4 mL {[substrate (0.5 mmol, 0.125 M)/[Rh]/L = 1:0.01:0.011]}. The reaction went with >99% conversion unless otherwise stated.
[b]Enantiomeric excesses were determined by chiral HPLC using a (S,S)-whelk-o1 column.
[c]The absolute configuration was assigned by comparison of optical rotation with reported data.

TABLE 9

Asymmetric Hydrogenation of Enamides by a Rhodium-bisphosphine Complex[a]

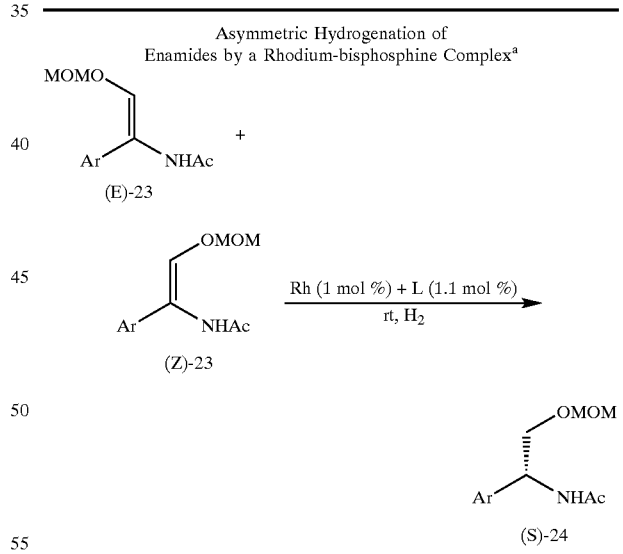

| Entry (%) | Substrate | Ar | Ligand | ee[b] | Config.[c] |
|---|---|---|---|---|---|
| 1 | 23a | $C_6H_5$ | 13a | 98 | S |
| 2 | 23a | $C_6H_5$ | 13b | 98 | R |
| 3 | 23b | p-$CH_3C_6H_4$ | 13a | 99 | S |
| 4 | 23b | p-$CH_3C_6H_4$ | 13b | 98 | R |
| 5 | 23c | p-$MeOC_6H_4$ | 13a | 96 | S |
| 6 | 23c | p-$MeOC_6H_4$ | 13b | 96 | R |
| 7 | 23d | p-$ClC_6H_4$ | 13a | 97 | S |
| 8 | 23d | p-$ClC_6H_4$ | 13b | 98 | R |
| 9 | 23e | p-$FC_6H_4$ | 13a | 99 | S |
| 10 | 23e | p-$FC_6H_4$ | 13b | 98 | R |

TABLE 9-continued

Asymmetric Hydrogenation of
Enamides by a Rhodium-bisphosphine Complex[a]

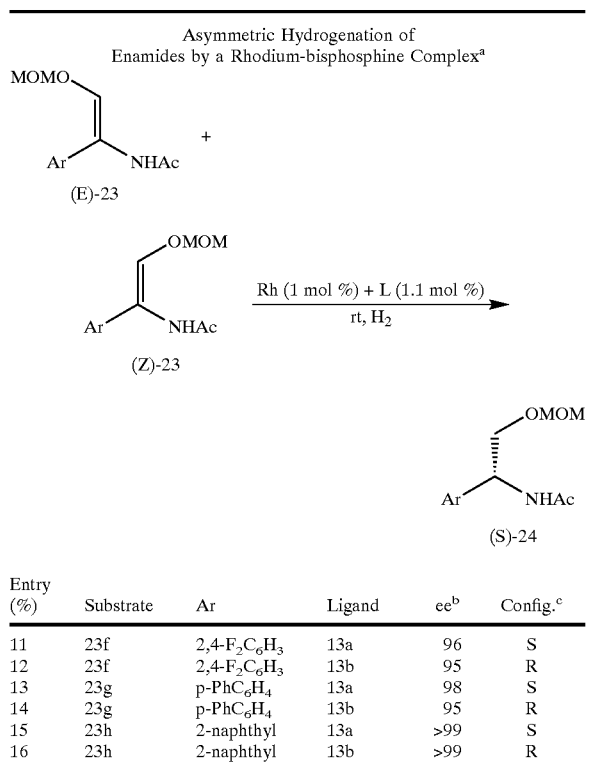

| Entry (%) | Substrate | Ar | Ligand | ee[b] | Config.[c] |
|---|---|---|---|---|---|
| 11 | 23f | 2,4-F$_2$C$_6$H$_3$ | 13a | 96 | S |
| 12 | 23f | 2,4-F$_2$C$_6$H$_3$ | 13b | 95 | R |
| 13 | 23g | p-PhC$_6$H$_4$ | 13a | 98 | S |
| 14 | 23g | p-PhC$_6$H$_4$ | 13b | 95 | R |
| 15 | 23h | 2-naphthyl | 13a | >99 | S |
| 16 | 23h | 2-naphthyl | 13b | >99 | R |

[a]The reaction was carried out at room temperature under 15 bar bar of H$_2$ for 36 h. The catalyst was prepared in situ by stirring a solution of Rh(NBD)$_2$SbF$_6$ and the bisphosphine ligand L in CH$_2$Cl$_2$ 4 mL {[substrate (0.5 mmol, 0.125 M)/[Rh]/L = 1:0.01:0.011]}. The reaction went with >99% conversion unless otherwise stated.
[b]Enantiomeric excesses were determined by chiral HPLC using a (S,S)-whelk-o1 column.
[c]The absolute configuration was assigned by comparison of optical rotation with reported data.

Under the standard reaction conditions, a variety of α-arylenamides 23 with a MOM-protected β-hydroxyl group were subjected to the hydrogenation catalyzed by Rh-13b or Rh-13a catalysts (Table 9). All of these substrates were hydrogenated with high enantiomeric excess (95~>99%) regardless of whether the substrate was bearing electron donating or withdrawing substituent in the aryl rings. These results obviously indicated that this Rh catalytic system provided an efficient approach to β-amino alcohols.

The β-amino alcohol moiety is a common building block in naturally occurring and synthetic molecules. Synthetic methods for their preparation are well documented. This reaction is not very sensitive to the solvents (entries 1–4) and hydrogen pressure (entries 2, 3 and 5–8).

It is clear from the above that the chiral ligands with 1,4-dioxane backbone can be prepared easily using Ley's "CDA" and "Dispoke" methodology as the key step. The Rh catalysts with chiral 1,4-diphenylphosphines 13a, 13b and 18 are very effective for the asymmetric hydrogenation of enamides and MOM-protected β-hydroxyl enamides providing a wide range of chiral amines and β-amino alcohols with high optical purity. Further investigation to the application of this catalytic system in asymmetric synthesis and understanding about the roles of the 1,4-dioxane backbone in stabilizing the chelate conformation are now undergoing, and the results will be reported in due course.

(2R,3R,5S,6S)-2,3-diethoxy-2,3-dimethyl-5,6-bis(hydroxymethyl)[1,4]dioxane 20

(±)-10-Camphorsulfonic acid (1.1 g, 4.9 mmol) was added to a solution of L-diethyl tartrate (10.1 g, 49 mmol), 2,3-dibutanone (5.1 g, 59 mmol) and dry triethyl orthoformate (30 mL, 180 mmol) in dry ethanol (200 mL). The reaction was heated under reflux for 16 h after which the mixture was neutralized with triethyl amine (5 mL). The solvent was removed under reduced pressure and the residue was purified by a small plug to give an oil. This oil obtained above was reduced using LiAlH$_4$ in THF and usual workup gave a white solid which was further purified by recrystallization from hexanes/ether in 68% yield. The analytical data were identical to the sample prepared earlier by the different route.

(2R,3R,5S,6S)-2,3-dimethoxy-2,3-dimethyl-5,6-bis(((methanesulfonyl)oxy)methyl)[1,4]dioxane 21

To a solution of diol 20 (2.36 g, 10.0 mmol) and triethylamine (4.9 mL, 35.0 mmol) in CH$_2$Cl$_2$ (30 mL) was added drop wise a solution of methanesulfonyl chloride (2.4 mL, 30.0 mmol) in CH$_2$Cl$_2$ (10 mL) at 0° C. After 30 min at 0° C., the reaction mixture was stirred for additional 30 min at room temperature, then quenched by saturated aqueous ammonium chloride solution (30 mL). The aqueous layer was extracted with CH$_2$Cl$_2$ (3×30 mL) and the combined organic solution was dried over Na$_2$SO$_4$. After evaporation of the solvent, the residue was purified by a flash chromatography on silica gel eluted with CH$_2$Cl$_2$/ethyl ether (8/2) to give a white solid 3.80 g in 97% yield: mp 90–2° C. $[\alpha]^{24}_D$=−121.8 (c 1.0, CHCl$_3$). $^1$H NMR (CDCl$_3$, 360 MHz) 84.39–4.27 (m, 4H), 4.01–3.90 (m, 2H), 3.21 (s, 6H), 3.07 (s, 6H), 1.24 (s, 6H); $^{13}$C NMR (CDCl$_3$, 90.56 MHz) 699.1, 68.7, 66.4, 48.1, 37.7, 17.1. HRMS calcd for C$_{11}$H$_{21}$O$_9$S$_2$ (M—OCH$_3$)$^+$: 361.0627; found: 361.0612.

(6R,7R,14R,15R)-1,8,13,16-Tetraoxa-dispiro[5,0,5,4]-14,15-bis((diphenylphosphanyl)methyl) hexadecane 18

The phosphine 18 was prepared according to the procedure for the synthesis of 13. A flash chromatography on silica gel eluted with hexanes/CH$_2$Cl$_2$/ethyl acetate (80/20/1) gave a white solid in 53% yield: mp 105–6° C. $[\alpha]^{24}_D$=−94.3° (c 0.8, CHCl$_3$). $^1$H NMR (CDCl$_3$, 360 MHz) δ7.44–7.20 (m, 20H), 3.80–3.76 (m, 2H), 3.38–3.30 (m, 4H), 2.30–2.22 (m, 4H), 1.55–1.18 (m, 12H); $^{13}$C NMR (CDCl$_3$, 90.56 MHz) δ138.3 (d, J=8.2 Hz), 137.5 (d, J=9.0 Hz), 133.5 (d, J=19.7 Hz), 132.5 (d, J=17.9 Hz), 129.2, 128.6 (d, J=7.4 Hz), 128.5, 128.3 (d, J=6.9 Hz), 96.3, 69.9 (t, J=10.5 Hz), 60.7, 30.5 (d, J=11.6 Hz), 28.5, 24.93, 17.8. $^{31}$P NMR (CDCl$_3$) δ−18.6 ppm. HRMS calcd for C$_{38}$H$_{43}$O$_4$P$_2$ (MH$^+$): 625.2637; found: 625.2622.

General Procedure for Asymmetric Hydrogenation

To a solution of [Rh(COD)$_2$]PF$_6$ (2.1 mg, 0.0045 mmol) in methanol (4 mL) in a glovebox was added bisphosphine 13b (0.10 mL of 0.05 M solution in toluene, 0.005 mmol). After stirring the mixture for 10 min, substrate (0.5 mmol) was added. The hydrogenation was performed at room temperature under 45 psi of hydrogen for 24 h. After the hydrogen was released, the reaction mixture was passed through a short silica gel column to remove the catalyst. The enantiomeric excess was measured by capillary GC or HPLC directly without any further modification. The absolute configuration of the products was determined by comparing the observed rotation with the reported value.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A ligand on selected from the group consisting of compounds represented by II through VII and IX through XI:

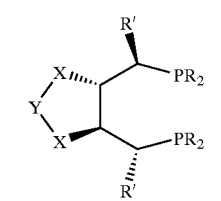

II

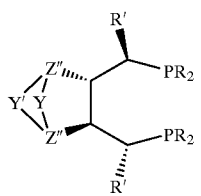

III

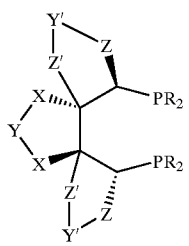

IV

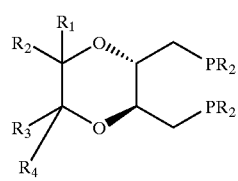

V

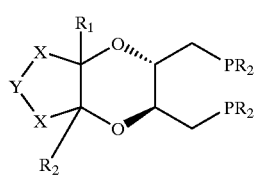

VI

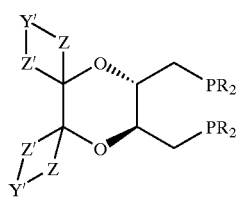

VII

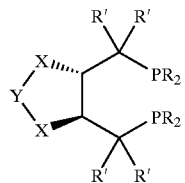

IX

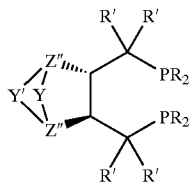

X

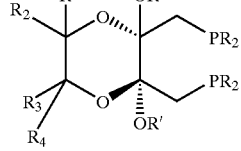

XI said ligand being attached to a support material through physical interactions or linked to said support material by a linker group;

wherein R' is selected from the group consisting of: alkyl, aryl, substituted alkyl, substituted aryl, hydroxy, alkoxy, aryloxy, amino, alkylamino, dialkylamino, arylamino, diarylamino, alkylarylamino and amido;

wherein each X, Z and Z' is independently selected from the group consisting of: O, S, $SO_2$, and SO;

wherein each Z" is independently selected from the group consisting of: CH, and CR;

wherein each $R_1$, $R_2$, $R_3$ and $R_4$ is independently selected from the group consisting of: H, alkyl, aryl, substituted alkyl, substituted aryl and OR;

wherein Y is selected from the group consisting of: O and $SO_2$, and Y' is selected from the group consisting of: O, CO, $C(OR)_2$, CH(OR), $CH_2$, CHR, $CR_2$, $SO_2$, —$(CH_2)_n$— wherein n is 0 or an integer from 1 to 8, —$(CH_2)_nQ(CH_2)_m$— wherein each n and m is independently an integer from 1 to 8, divalent phenyl, substituted divalent phenyl, 2,2'-divalent-1,1'-biphenyl, substituted 2,2'-divalent-1,1'-biphenyl, 2,2'-divalent-1, 1'-binaphthyl, substituted 2,2'-divalent-1,1'-binaphthyl, 1,1'-ferrocene, substituted 1,1'-ferrocene, wherein the substituent in each of said substituted divalent phenyl, biphenyl, binaphthyl and ferrocene is one or more moiety each independently selected from the group consisting of: alkyl, aryl, aralkyl, alkaryl, alkenyl, alkynyl, F, Cl, Br, I, OH, OR, SH, SR, COOH, COOR, $SO_3H$, $SO_3R$, $PO_3H_2$, $PO_3HR$, $PO_3R_2$, $NH_2$, NHR, $NR_2$, $PR_2$, $AsR_2$, $SbR_2$ and nitro; and wherein each R is independently selected from the group consisting of: alkyl, aryl, substituted alkyl, substituted aryl, fluoroalkyl, perfluoroalkyl and —$CR'_2(CR'_2)_qQ(CR'_2)_pR'$ wherein each q and p is independently an integer from 1 to 8, Q is selected from the group consisting of: O, S, divalent aryl, divalent fused aryl, divalent 5-membered ring heterocycle and divalent fused heterocycle.

2. The ligand of claim 1, wherein said support material is selected from the group consisting of: a polymer support and an inorganic support.

3. The ligand of claim 2, wherein said polymer support is selected from the group consisting of: polystyrene, polyacrylate, resin, PEG, MeO-PEG, dendritic polyester and dendritic polyenamide.

4. The ligand of claim 2, wherein said inorganic support is selected from the group consisting of: silica, alumina, zeolite and molecular sieve and wherein said ligand is attached to said inorganic support through physical interactions.

5. The ligand of claim 2, wherein said ligand is linked to a support material by a linker group selected from the group consisting of:

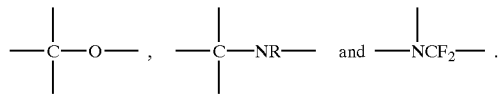

6. The ligand of claim 1, wherein said substituent in each of said substituted divalent phenyl, biphenyl, binaphthyl and ferrocene is one or more water soluble functional groups selected from the group consisting of: sulfonic, phosphoric and carboxylic acid groups.

7. An (R,S,S,R)-DIOP* ligand represented by the formula:

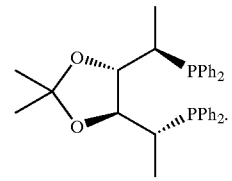

(R, S, S, R)-DIOP*

8. The ligand of claim 2, wherein said ligand is linked to a support material by a linker group selected from the group consisting of: $NH(CH_2)_nSi(OEt)_3$, $CO(CH_2)_nSi(OEt)_3$, $(CH_2)_nSi(OEt)_3$, wherein n=1 to 8.

* * * * *